United States Patent
Shikakubo et al.

[19]

[11] Patent Number: 5,943,765
[45] Date of Patent: Aug. 31, 1999

[54] DEVICE FOR MAKING STITCHING THREAD ATTACHED WITH A NEEDLE

[75] Inventors: Kenji Shikakubo; Keiichi Yokohiki, both of Sakaimachi; Gennai Yanagisawa, Matsumoto, all of Japan

[73] Assignee: Kabushiki Kaisha Azwell (Azwell Inc.), Osaka-fu, Japan

[21] Appl. No.: 08/945,059

[22] PCT Filed: Feb. 13, 1997

[86] PCT No.: PCT/JP97/00380

§ 371 Date: Oct. 14, 1997

§ 102(e) Date: Oct. 14, 1997

[87] PCT Pub. No.: WO97/29692

PCT Pub. Date: Aug. 21, 1997

[30] Foreign Application Priority Data

Feb. 16, 1996 [JP] Japan ................................. 8-029230

[51] Int. Cl.$^6$ .............................. B23P 21/00; B23P 11/00
[52] U.S. Cl. ............................... 29/705; 29/788; 29/796; 29/243.517; 29/283.5; 83/153; 83/950
[58] Field of Search ........................ 29/243.5, 243.517, 29/283.5, 515, 516, 517, 564.6, 705, 711, 715, 783, 785, 786, 788, 792, 793, 796, 818, 712, 822; 606/224, 225, 226; 83/151, 153, 154, 950

[56] References Cited

U.S. PATENT DOCUMENTS 4,922,904  5/1990  Uetake et al. .

5,473,810  12/1995  Demarest et al. .
5,487,212  1/1996  Demarest et al. .

FOREIGN PATENT DOCUMENTS 63-212028  9/1988  Japan .
460654  9/1992  Japan .

Primary Examiner—David P. Bryant
Attorney, Agent, or Firm—Jordan and Hamburg LLP

[57] ABSTRACT

An object of this invention is to provide a needle attached suture manufacturing apparatus, with a simple construction and reduced cost, capable of assuredly inserting the lead end of a suture in an insertion hole formed in the end of a needle before the end of the needle is swaged. In order to accomplish the above object, a needle swaging device 20 of this apparatus includes die support members 101 and 102 on which swaging dies 111 and 112 are mounted to be movable toward and away from each other. Suture guide plates 95 and 96 are mounted on the die support members 101 and 102 and are formed with guide grooves 95a and 96b, respectively. Before a swaging operation of the needle end by the swaging dies 111 and 112, the suture guide plates 95 and 96 move to a contact state or to a close contact state with each other when the swaging dies 111 and 112 are set to a pre-swaging position in contact with or in close contact with the end of the needle. In this state, the guide grooves 95a and 96b define a tapered (funnel-like) hole for guiding the insertion of the suture lead end into the insertion hole at the end of the needle.

43 Claims, 15 Drawing Sheets

DEVICE FOR MAKING STITCHING THREAD ATTACHED WITH A NEEDLE

BACKGROUND OF THE INVENTION

This invention relates to an apparatus for manufacturing needle attached sutures, in which the end of a surgical needle or its equivalent is swaged in a state that the lead end of a suture is inserted in an insertion hole formed in the end of the needle to attach the suture to the needle.

Recently, in the field of medical industry, there have been marketed sterilized needle attached sutures (sutures attached with needles) in which the lead end of a suture is fixedly attached to a needle. Such needle attached suture can be produced by retaining a needle in a certain orientation, and swaging the end of the needle after inserting the lead end of a suture in an insertion hole formed in the end of the needle (as disclosed in, e.g., Japanese Examined Patent Publication No. HEI 4-66579).

The diameter of the suture and the corresponding insertion hole of the needle is very small (generally, in the range of 260 to 400 μm). Accordingly, it is difficult to assuredly insert the lead end of the suture into the insertion hole of the needle. The above publication discloses a guide member formed with a tapered guide hole whose diameter decreases approaching the insertion hole of the needle. The guide member is designed to guide the lead end of the suture toward the insertion hole of the needle in order to facilitate insertion of the lead end of the suture into the insertion hole of the needle.

The above prior art apparatus, contrary to the motivation of enhancing smooth insertion of the suture into the insertion hole of the needle, may hinder the smooth insertion of the suture in the case that the axis of the guide hole of the guide member is misaligned from the axis of the insertion hole of the needle. Accordingly, to effectively utilize the guide member, it is required to accurately position the guide hole of the guide member relative to the insertion hole of the needle.

However, the guide member of the above apparatus is disposed relatively far away from the insertion hole of the needle with the swaging dies interposed therebetween, and accordingly it is difficult to accurately align the guide hole of the guide member with the insertion hole of the needle. In addition, the swaging dies also need to be positioned accurately to obtain a desired swaging force when the end of the needle is to be swaged after the step of inserting the suture in the insertion hole of the needle. However, it takes a great deal of time and care to accurately position the swaging dies and the guide member relative to the end of the needle separately.

Japanese Examined Patent Publication No. HEI 4-60654 discloses an arrangement in which the location of the needle and suture is monitored through an image processing by a TV camera and an insertion operation of the suture into the needle is conducted referring to the monitored image. This arrangement needs a complicated and large-scaled facility and hence increase of the facility cost is inevitable.

SUMMARY OF THE INVENTION

In view of the above, an object of the invention is to provide a needle attached suture manufacturing apparatus, with a simple construction and reduced cost, capable of securely inserting the lead end of a suture in an insertion hole formed in the end of a needle with accuracy before swaging the end of the needle with the suture.

To solve the above problems, the invention has adopted the following arrangement.

The invention is directed to an apparatus for manufacturing a needle attached suture in which an end of a needle is swaged with a lead end of a suture inserted in an insertion hole formed in the end of the needle to combine the suture with the needle. The apparatus comprises: needle retaining means for retaining the needle with at least the end thereof left unretained; insertion means for inserting the lead end of the suture into the insertion hole of the needle retained by the needle retaining means; a pair of swaging, dies for swaging at a swaging position, from opposite directions the end of the needle with the suture inserted in the insertion hole of the needle; die support members for supporting the swaging dies respectively; swaging drive means for moving the die support members in a direction to move the swaging dies toward and away from each other; and suture guide members each provided between the insertion means and the swaging die and formed with a hollow portion so as to form a tapered guide hole when the suture guide members are brought in contact with each other, the tapered guide hole having a diameter decreasing in a suture insertion direction. The suture guide members are provided on the respective die support members and are so set that the suture guide members are positioned in contact or in close proximity with each other when the die support member is moved to a pre-swaging position at which the swaging dies are in contact or in close proximity with the end of the needle, and before the swaging position.

With this arrangement, when the die support members are positioned at the pre-swaging position where the swaging dies come into contact with or in close proximity with the end of the needle, the suture guide members (suture guide means) mounted on the die support members come into contact with or in close proximity with each other. The tapered (funnel-like) suture guide hole is thereby defined in front of the needle end. The suture guide hole provides for a smooth insertion of the lead end of the suture into the insertion hole of the needle.

Since the suture guide member is mounted on the common die support member with the swaging die as one-piece unit, the suture guide member is positioned relative to the insertion hole of the needle assuredly. Accordingly, the suture guide member provides accurate and reliable guiding of the lead end of the suture into the insertion hole of the needle.

Further, since the swaging die also requires precise positioning to obtain a desired swaging force and is mounted on the common die support member together with the suture guide member, the mounting position of the suture guide member can be adjusted finely together with positioning of the swaging die. Accordingly, compared to the conventional arrangement in which positioning of the swaging dies and positioning of the suture guide members are conducted separately, the apparatus can be assembled easily.

Preferably, the apparatus may further comprise swaging control means for positioning the die support member at the pre-swaging position before the end of the needle is swaged. Thereby, insertion operation of the suture and swaging operation can be automated.

Swaging drive means for driving the die support members is not limited to any specific one. However, preferably, at least one of the die support members may be rotatable about an axis extending in a direction orthogonal to an aligned direction of the swaging dies. The swaging drive means may include a cam interposed between the die support members, and cam drive means for rotating the cam and the cam may be configured such that the swaging dies move toward and away from each other in association with a rotation of the cam.

With this arrangement, the swaging force by the swaging dies and the pre-swaging position can be adjusted finely by merely varying the rotational amount of the cam.

The suture guide members may be fixedly mounted on the die support members to restrict a movement of the suture guide members relative to the die support members. In this case, however, if the suture guide members have already come into contact with each other when the die support members reach the pre-swaging position, the die support members cannot move closer to each other any more, resulting in an incapability of performing a swaging ation that follows. Accordingly, in the above arrangement, it is required to set the position of the die support members with a small clearance left therebetween when the die support members are set to the pre-swaging position. However there is a possibility that the lead end of the suture may be trapped in the clearance.

Preferably, however, at least one of the suture guide members may be provided on the die support member to be movable relative to the die support member in a direction substantially parallel with the needle swaging direction, biasing means may be provided to bias the movable one of the suture guide members to the non-movable one, and the suture guide members may be set to come into contact with each other when the die support member is positioned to the pre-swaging position.

With this arrangement, the suture guide members can come into contact with each other when the die support members are set to the pre-swaging position, and then, the swaging dies can further come closer to each other in accordance with a further approaching movement of the die support members relative to the suture guide members after the pre-swaging position, while assuredly guiding the lead end of the suture toward the insertion hole of the needle in this state. Thereby, the end of the needle can be swaged with a desired swaging force. In other words, this arrangement can attain accurate and reliable guiding of the lead end of the suture into the insertion hole of the needle since the suture guide members can surely come into contact with each other at the pre-swaging position, and also realize a desirable swaging operation that follows.

More preferably, the relative position of the swaging die may be adjustable with respect to the die support member in the needle swaging direction. Thereby, the swaging force can be finely adjusted by changing the mounting position of the swaging die.

More preferably, the die support member may be formed with a hollow portion extending in the needle swaging direction to restrict a displacement of the swaging die in a direction orthogonal to the needle swaging direction when the swaging die is fitted in the hollow portion.

With this arrangement, the relative position of the swaging die in the needle swaging direction can be adjusted, while restricting the displacement of the swaging die in the direction orthogonal to the needle swaging direction.

Preferably, the swaging die may be formed with a bolt insertion hole; the suture guide member may be formed with a spacer insertion hole at a position corresponding to the bolt insertion hole; a tubular spacer having the outer diameter thereof smaller than the diameter of the spacer insertion hole and the axial length thereof greater than the thickness of the suture guide member may be fitted in the spacer insertion hole; and a die fixing bolt may be inserted in the bolt insertion hole of the swaging die and in the spacer placed in the spacer insertion hole of the suture guide member and engaged with the die support member to fix the spacer and the swaging die on the die support member. The diameter of the die fixing bolt is smaller than the inner diameter of the spacer and the diameter of the bolt insertion hole.

With this arrangement, in a state that the swaging die is fixed on the die support member by the die fixing bolt, the suture guide member can be moved relative to the die support member a dimension corresponding to the gap between the outer circumferential size of the spacer and the inner circumferential size of the spacer insertion hole. Accordingly, fixation of the swaging dies and mounting of the suture guide members on the die support members can be facilitated with a simple construction using the die fixing bolt and the spacer.

More preferably, the die support member may be provided with pushing means for pushing the die support member from outward an amount corresponding to an external force applied thereto. Thereby, the pushing means can fix the swaging die at a certain position against the reaction force resulting from the swaging operation. Accordingly, a desired swaging force can be obtained more stably.

Preferably, the insertion means may hold a certain portion of the suture except the lead end thereof in a specified direction and transport the suture toward the suture guide means to insert the lead end of the suture into the insertion hole at the end of the needle through the guide hole of the suture guide means.

More preferably, the apparatus may further comprise aligning means provided between the insertion means and the suture guide means for nipping the lead end of the suture to align the position of the lead end of the suture with the insertion hole of the needle. Thereby, the lead end of the suture can be more smoothly inserted in the insertion hole of the needle.

In this case, if the aligning means (positioning means) is constructed to nip the lead end of the suture in a direction orthogonal to the holding direction of the insertion means, the alignment of the lead end of the suture with the insertion hole of the needle can be performed more precisely, since the lead end of the suture has been aligned to a certain extent in the holding direction of the insertion means.

Preferably, the apparatus may further comprise load supplier means for loading a specified stationary load on the suture combined with the needle in a state that the needle retaining means holds the needle attached suture.

With this arrangement, inspection of the needle attached suture can be efficiently executed in a state that the needle retaining means holds the needle attached suture. This eliminates an additional operation of transferring the needle attached suture to another device for inspection.

Preferably, the load supplier means may include weight link means for linking a weight member having a weight corresponding to the specified stationary load to the suture, suture manipulator means for lifting an intermediate portion of the suture to a level substantially horizontal to a combined portion of the suture and the needle, and weight release means for setting the weight member to a hung state from a supported state where the weight member is supported on the release means by being gradually lowered away from the weight member.

Alternatively, without the weight release means, the load supplier means may include suture manipulator means for setting the weight member from a supported state where the weight member is supported on a base member to a hung state by lifting an intermediate portion of the suture upward to gradually hang the weight member above the base member.

With these arrangements, a certain stationary load can be surely loaded on the suture with a simple construction, without generating a dynamic load such as impact force.

Throughout the specification, the recitation "being gradually lowered away from the weight member" or "gradually hang the weight member above the base member" means that the weight release means is lowered or the weight member is hung at a sufficiently low speed that does not result in producing a dynamic load such as impact force exceeding the stationary load corresponding to the weight of the weight member during moving away from the weight member or hanging the weight member.

More preferably, the apparatus may further comprise discharge means for transferring the suture combined with the needle to a specified discharge position after it is confirmed that loading the stationary load does not pull out the suture from the needle. Thereby, quality control of needle attached sutures can be automated speedily.

BEST MODE FOR CARRYING OUT THE INVENTION

One of the preferred embodiments according to the invention is described along with the drawings.

Figure 1:
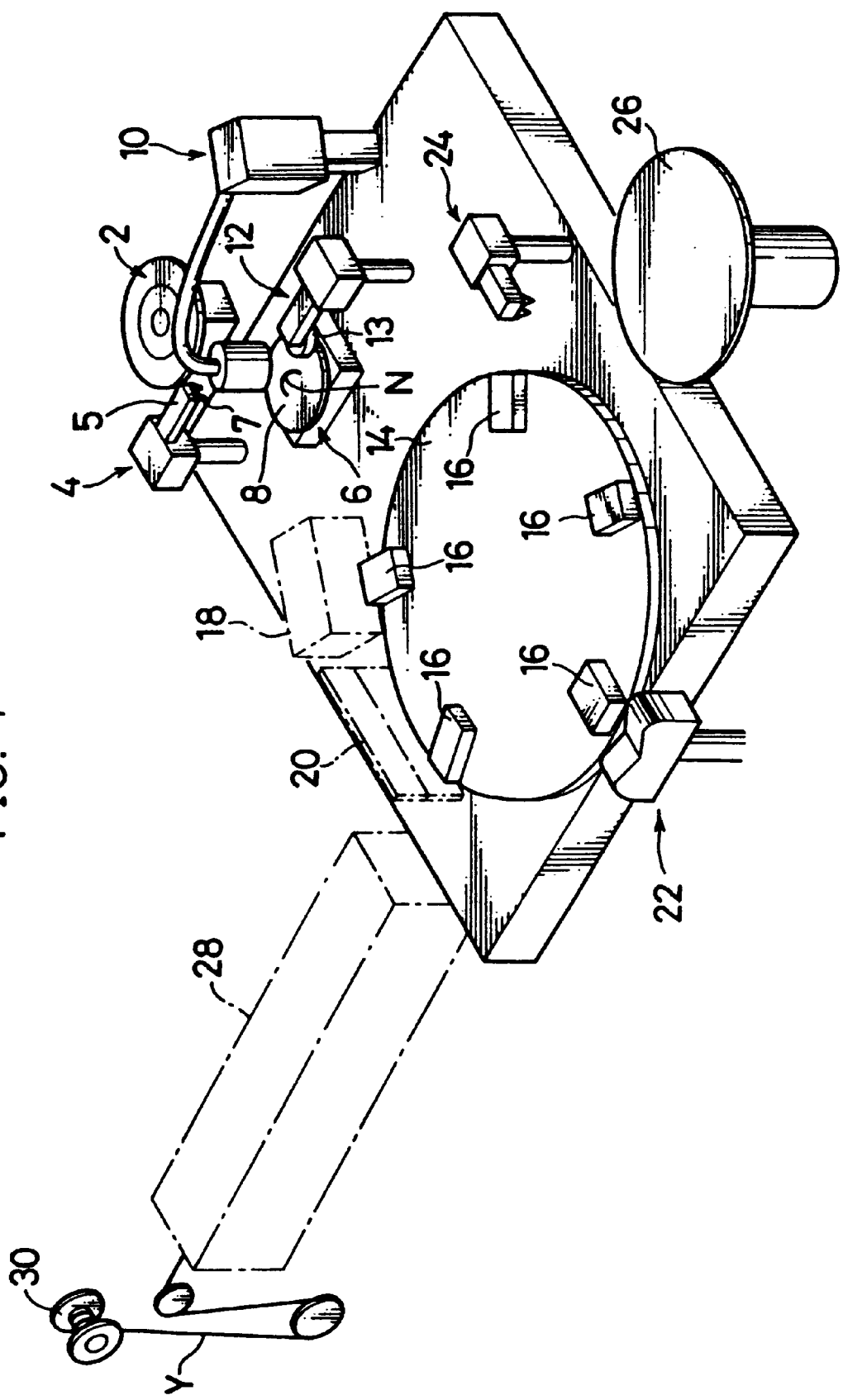
FIG. 1 is a perspective view of an embodiment of an arrangement of a needle attached suture manufacturing apparatus according to the invention.
Figure 2:
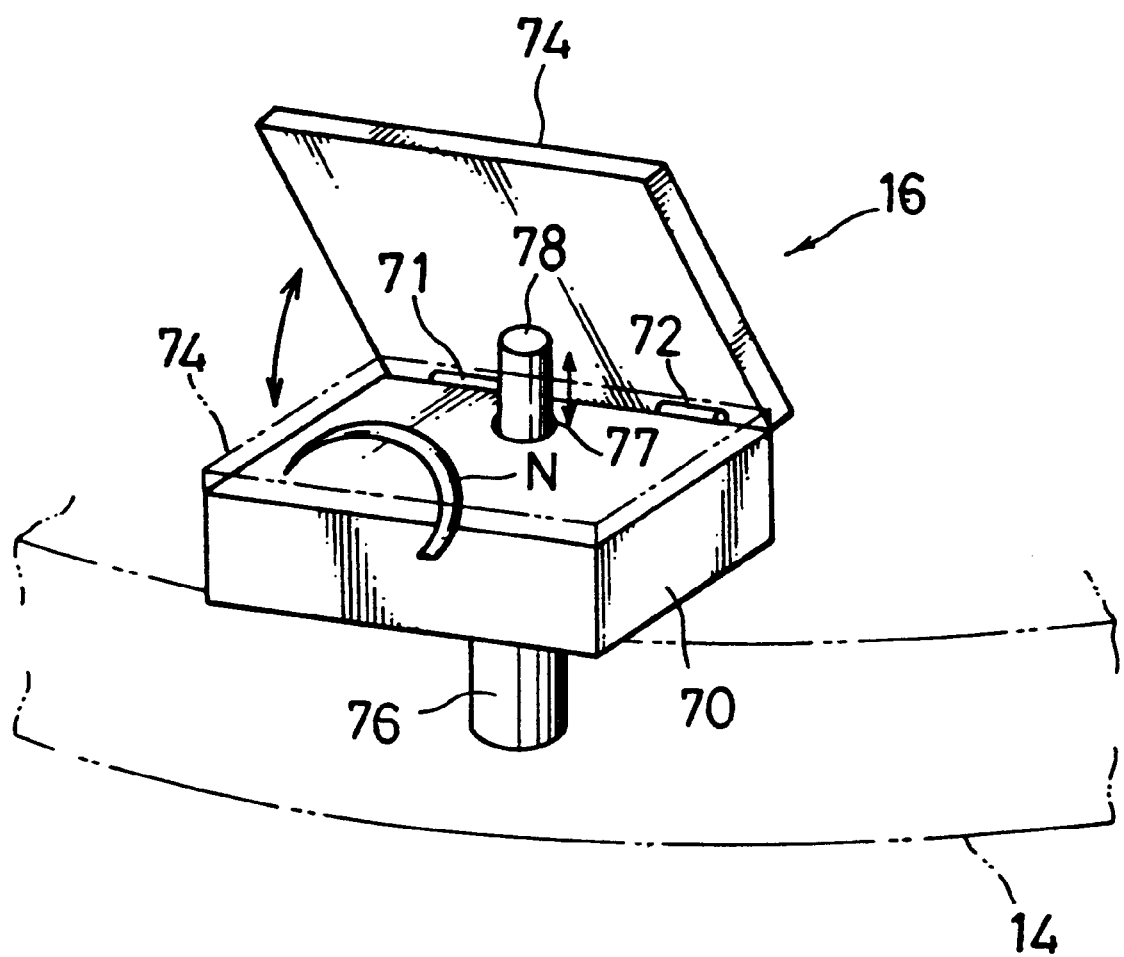
FIG. 2 is a perspective view of a needle retaining unit in the manufacturing apparatus.

FIGS. 1 and 2 show an apparatus for manufacturing needle attached sutures. The apparatus comprises a needle supply device 2, a needle transport device 4, a needle orientation adjuster device 6, a needle pickup device 12, a turntable 14, a needle end adjuster device 18, a needle swaging device 20, a pull test device 22, a needle discharge device 24, a needle discharge table 26, and a suture supply device 28.

The needle transport device 4 is adapted for picking up a needle N supplied to a predetermined position on the needle supply device 2 and for transporting the same to the needle orientation adjuster device 6. Note that the needle N handled by the needle attached suture manufacturing apparatus has a shape substantially curved into an arc and is formed with an insertion hole axially opened at an end thereof.

The needle orientation adjuster device 6 has an adjuster table 8 on which the needle N is to be placed, and an image recognizer 10 such as a CCD. The image recognizer 10 recognizes an image of the needle N placed on the adjuster table 8. The needle orientation adjuster device 6 is adapted for finely adjusting the position and the direction of the needle N placed on the adjuster table 8 to coincide the position and the direction of the recognized image with those of a target image, stored in advance, by horizontally moving and angularly displacing the adjuster table 8 according to needs.

The needle pickup device 12 is adapted for picking up the needle N whose position and direction have been finely adjusted on the adjuster table 8 and for supplying the same to a needle retaining unit 16 on the turntable 14.

The turntable 14 is driven to make turns on a base block and to be vertically movable, and is provided with a plurality of needle retaining units 16 along a circumference thereof. Each needle retaining unit 16 is provided to hold the needle N supplied from the needle pickup device 12 thereon. With an angular displacement of the turntable 14, the needle retaining unit 16 transports the needle N to the needle end adjuster device 18, the needle swaging device 20, the pull test device 22, and the needle discharge device 24 in this order.

The detailed arrangement of the needle retaining unit 16 is described with reference to FIG. 2. The needle retaining unit 16 has a retainer main body 70 in the form of rectangular parallelepiped. The retainer main body 70 is fixedly mounted on an upper surface of the turntable 14 at an outer circumference.

An openable plate 74 is rotatably mounted on a rear side (rear side in FIG. 2) of the retainer main body 70 via hinges 71 and 72. An air cylinder 76 is arranged upright at a lower portion of the retainer main body 70. An extendable rod 78 of the air cylinder 76 is inserted in a through hole 77 formed in the middle on the rear side of the retainer main body 70. The through hole 77 is formed in the longitudinal direction of the air cylinder 76. When the air cylinder 76 is activated to cause the extendable rod 78 to move upward from the through hole 77, the openable plate 74 is pushed upward by the upper end of the extendable rod 78 to be set to an opened state (see the solid line in FIG. 2). When the air cylinder 76 is activated to cause the extendable rod 78 to be retracted into the through hole 77, the openable plate 74 is set to a closed state by the weight thereof (see the phantom line in FIG. 2).

When the openable plate 74 is opened up, the needle N transported by the needle pickup device 12 is placed on the upper surface of the retainer main body 70 in a state that the end of the needle N is jutted forward (front side in FIG. 2) from the retainer main body 70. Subsequently, when the openable plate 74 is closed, the needle retaining unit 16 securely holds the needle N therein with the end thereof jutted outward.

The needle end adjuster device 18 is adapted for pushing the end of the needle N, held by the needle retaining unit 16 which is moved to a predetermined position via the turntable 14, to thereby finely adjust the end of the needle N. As is described below, the needle swaging device 20 is adapted for swaging the end of the needle N by upward and downward motion when a suture Y, supplied from the suture supply device 28, is inserted in an insertion hole at the end of the needle N which is securely held by the needle retaining unit 16. Thereby, the suture Y and the needle N are combined with a predetermined pressing (swaging) force to produce a needle attached suture.

The suture supply device 28 is constructed such that the suture Y, wound around a bobbin 30, is drawn out a certain length and cut to obtain a suture strand of the certain length and to insert the suture strand Y into the insertion hole of the needle N held by the needle retaining unit 16. The arrangement of the suture supply device 28 is described below in detail.

The pull test device 22 is adapted for inspecting whether the combining strength of the suture Y and the needle N is sufficient by exerting on the suture Y a stationary load (pull force) directing downward. The detailed arrangement of the pull test device 22 is described later.

The needle discharge device 24 is provided with a needle gripper at the lead end of a pivotal arm. The needle gripper picks up the needle N (combined with the suture Y) held on the needle retaining unit 16 and discharges the needle N onto the needle discharge table 26.

The arrangement of the suture supply device 28 is described in detail with reference to FIGS. 3 to 10.

Figure 3:
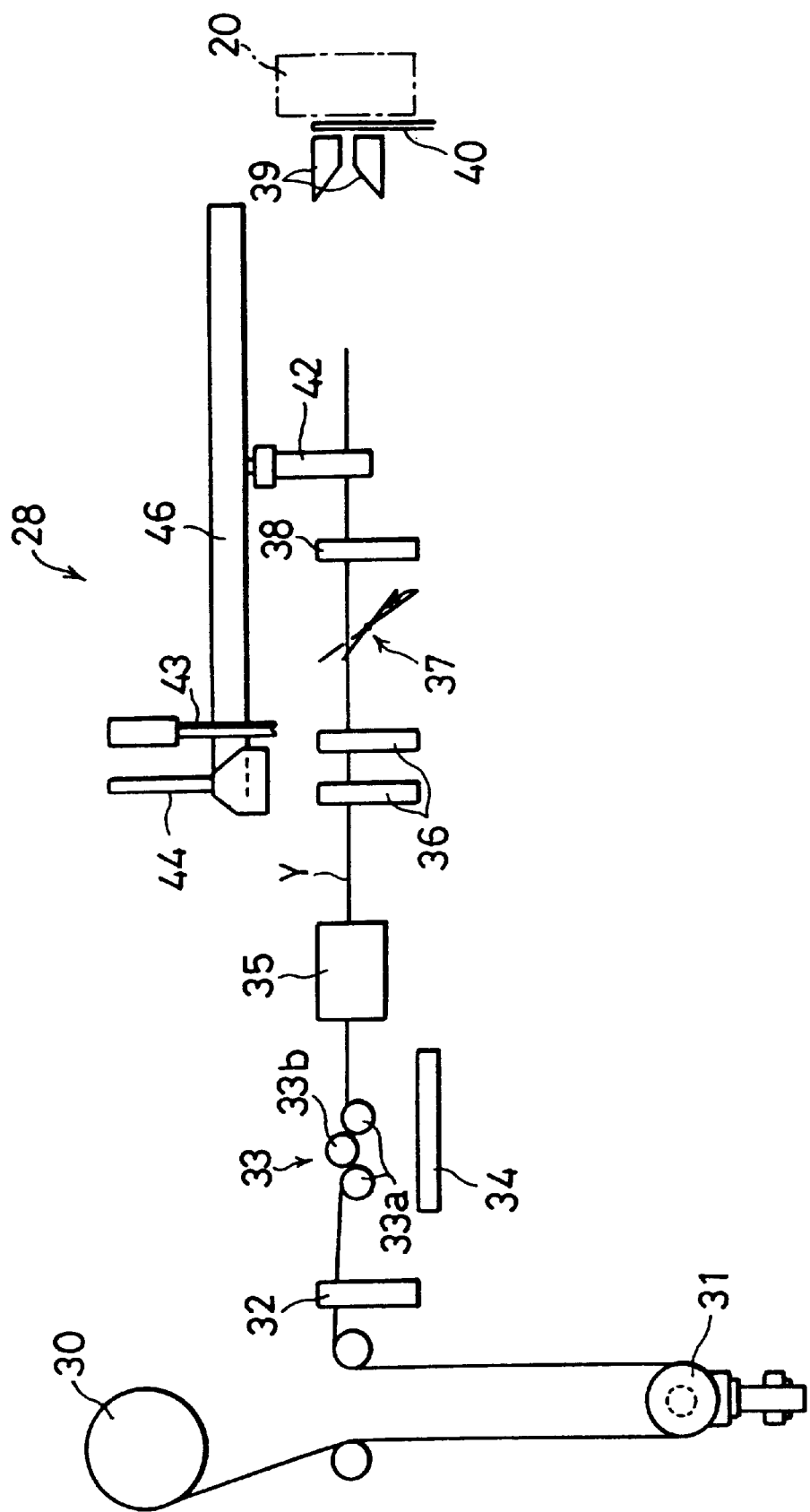
FIG. 3 is a schematic diagram showing an entire arrangement of a suture supply device in the manufacturing apparatus.

Referring to FIG. 3, the suture supply device 28 comprises, between the bobbin 30 and the swaging device 20 in this order, a dancer roller 31, a nipping device 32, a tension supplier 33, an electrostatic remover 34, a variation detector 35 for detecting a variation of the diameter of a suture, a pair of nipping devices 36 provided at front and rear sides with respect to the suture feed direction, a cutter 37, a center positioning/nipping device 38, an insertion/nipping device 39, and a nipping device 40 for use in centralizing the suture.

The suture supply device 28 further comprises a transport/holding device 42, a curing agent nozzle 43, and a dryer 44 that are movable in a direction parallel to the arranging direction (suture feed direction) of these devices.

The dancer roller 31 is mounted on the suture Y which is supplied from the bobbin 30. A weight of a certain weight hangs on the dancer roller 31 to constantly supply a certain tension force to the suture.

The holding means 32, 36, 38, and 42 nip the suture Y from the left and right direction (in FIG. 3, front and rear directions) at a certain timing. The nipping timing of the respective holding means is described below in detail.

The tension supplier 33 includes a pair of fixed rollers 33a, 33a, and a movable roller 33b interposed therebetween. When the movable roller 33b is moved down between the fixed rollers 33a and 33a to push the suture Y downward, a certain tension force is given to the suture Y.

The cutter 37 is a pair of scissors, e.g., "oriental" scissors, and is changeably moved to a cutting position (the position shown in FIG. 3) to nip the suture Y with the blades of the scissors and to a retracted position to retract obliquely downward away from the cutting position. When the cutter 37 is operated at the cutting position, the suture Y is obliquely cut at the cutting position.

The transport/holding device 42 is mounted on a movable member of a rodless cylinder (cylinder without a rod) 46, and reciprocates within a certain moving range from a start position which is located between the nipping device pair 36, and a position which is away from the start position a certain distance toward the needle swaging device 20 (distance corresponding to a target length at which the suture Y is to be cut).

The curing agent nozzle 43 moves within certain curing agent range between the cutting position of the cutter 37 and a position toward the nipping device pair 36 to a certain distance away from the cutting position. While moving within the curing agent range, the curing agent nozzle 43 applies a curing agent, such as an adhesive agent, to the surface of the suture Y. The dryer 44 is adapted for blowing heated air onto the curing agent coated on the surface of the suture Y to dry the coated curing agent.

The insertion/nipping device 39 is disposed at such a position as to vertically nip the suture Y. At a rear end (left end portion in FIG. 7) of the insertion/nipping device 39, there is formed a tapered portion 39a whose size is increased as approaching toward the rear end thereof. The tapered portion 39a is provided to smoothly guide insertion of the suture Y from the rear end.

Figure 5:
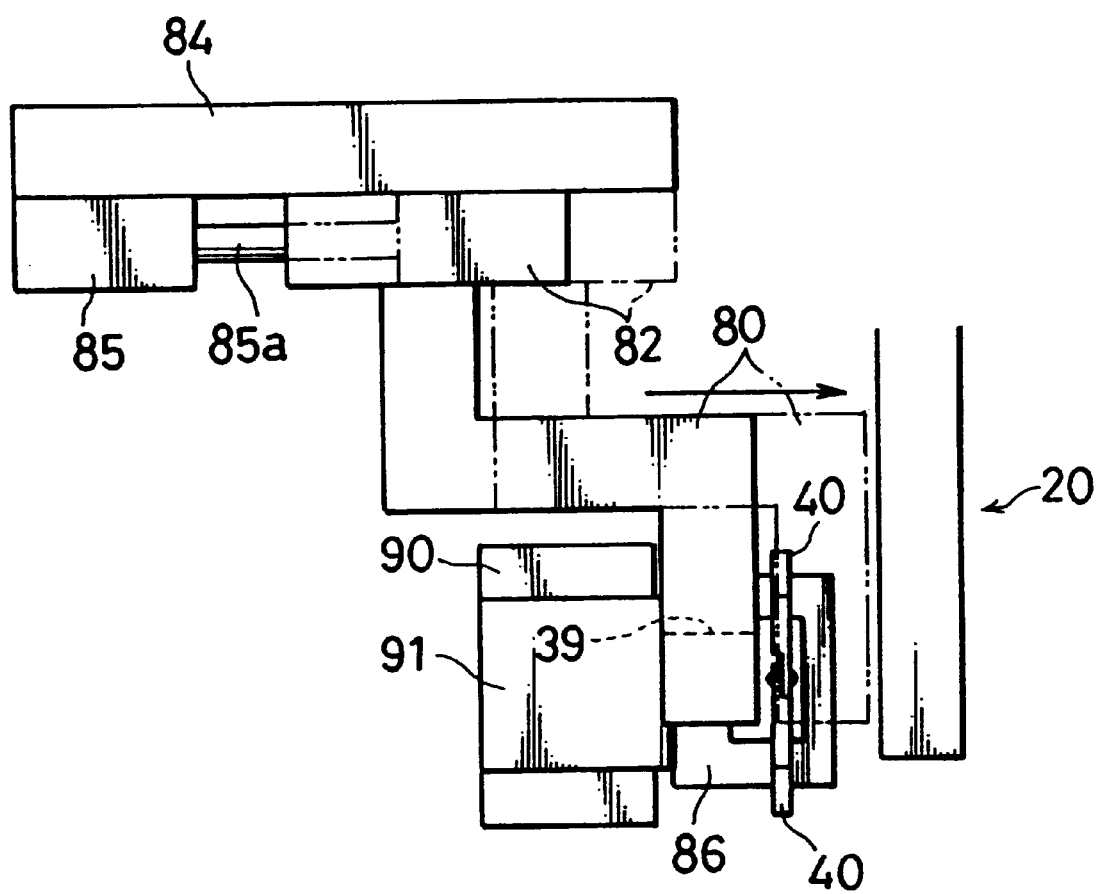
FIGS. 5 and 6 are respectively a plan view and a front view showing drive devices for use in inserting a suture and positioning the center of the suture while nipping the suture in the manufacturing apparatus.
Figure 6:
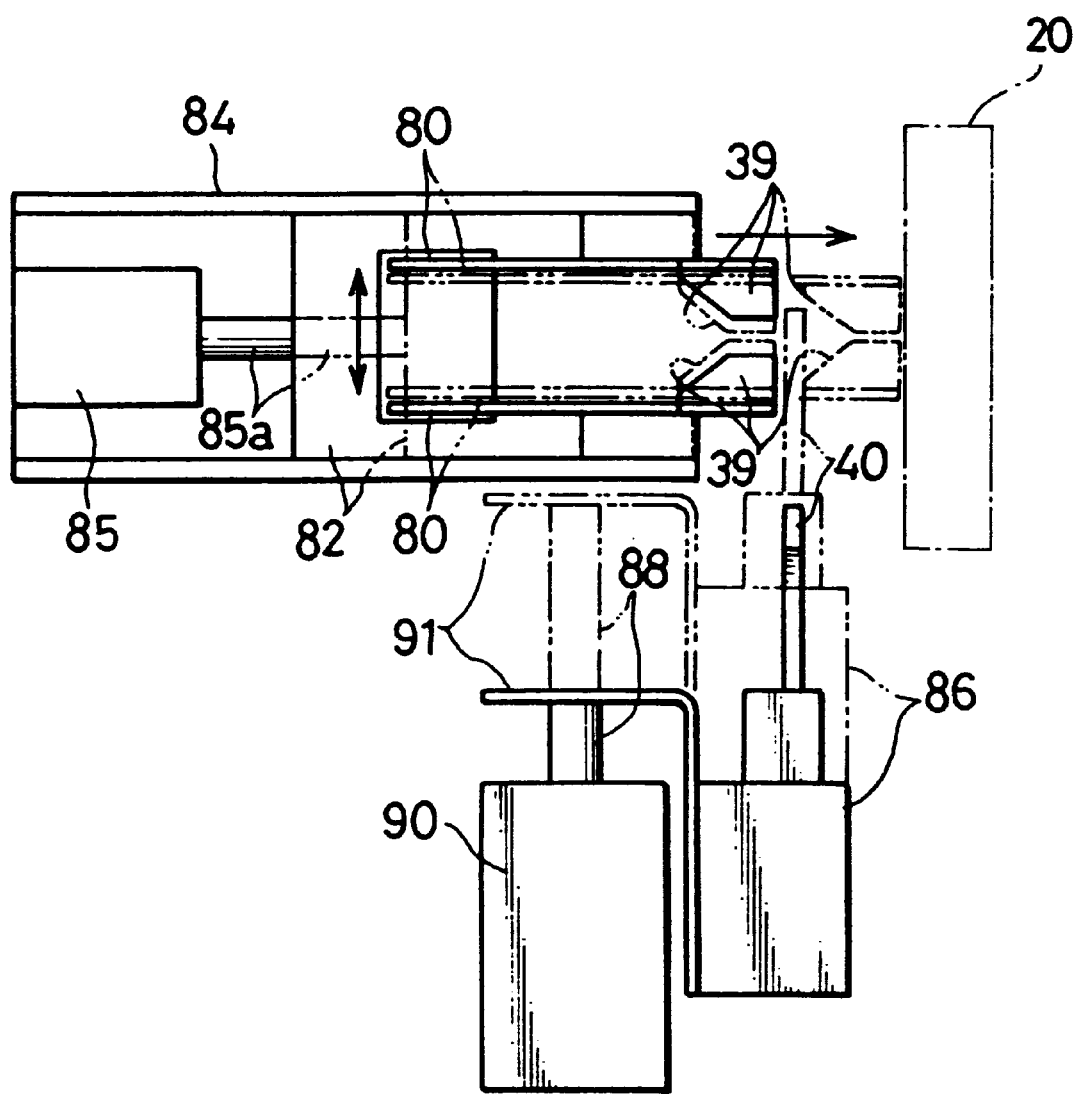

The insertion/nipping device 39 is driven by an insertion/nipping drive device shown in FIGS. 5 and 6. Upper and lower nipping portions of the insertion nipping/device 39 are fixed to a lead end of a pair of upper and lower support plates 80. A base end of the upper and lower support plates 80 is mounted on a clamp 82. The clamp 82 is internally provided with an air cylinder (not shown) for moving the upper and lower support plates 80 toward and away from each other. The insertion/nipping device 39 is actuated to move to a nipping position where the upper and lower nipping portions vertically nip the suture Y and to a release position where the nipping state is released in association with a movement of the upper and lower support plates 80.

The clamp 82 is slidably supported on a base member 84 to slide in a direction parallel to the longitudinal direction of the suture Y (left and right direction in FIGS. 5 and 6). An air cylinder 85 is fixedly mounted on the base member 84 horizontally. The clamp 82 is connected to the air cylinder 85 via an extendable rod 85a. When the air cylinder 85 is expanded and contracted, the clamp 82 reciprocates between the position shown by the solid line in FIG. 5 and the position shown by the phantom line in FIG. 5. The solid-line position corresponds to a suture receiving position of the insertion/nipping device 39 at which the device 39 can receive a portion of the suture near the lead end of the suture Y which has been carried by the transport/holding device 42 for nipping. The phantom-line position corresponds to a suture insertion position of the device 39 at which the lead end of the suture Y is nipped by the insertion/nipping device 39 and is inserted in an insertion hole formed in the end of the needle N which is held by the needle retaining unit 16.

A center positioning/nipping device 40 is provided between the insertion/nipping device 39 and the needle swaging device 20, and is connected to an air cylinder 86 at a lower end thereof. In accordance with an operation of the air cylinder 86, the center positioning/nipping device 40 is changed to a nipping position at which left and right nipping portions of the device 40 nip the suture Y from leftward and rightward directions as shown by the phantom line in FIG. 7, and a release position at which the nipping state is released as shown by the solid line in FIG. 7. When the center positioning/nipping device 40 is set to the nipping position to nip the lead end of the suture Y, the center position of the suture Y is finely adjusted to such a position at which the lead end of the suture Y can be inserted in the insertion hole of the needle N.

The air cylinder 86 is connected to an extendable rod 88 of an air cylinder 90 via a bracket 91. When the air cylinder 90 is charged and discharged, the center positioning/nipping device 40 is changed to the uppermost (shown by phantom line in FIG. 6) at which the device 40 is operable to horizontally nip the suture Y and the lowermost (shown by solid line in FIG. 6) at which the device 40 is retrieved below the suture Y.

The detailed arrangement of the needle swaging device 20 is described with reference to FIGS. 7 to 12. The needle swaging device 20 has a horizontal pin 100 supported on a base member, a lower die support member 101, and an upper die support member 102 each extending horizontally. The lower die support member 101 is formed with a projection 101*a* projecting upward from an upper surface in a middle between left and right ends thereof, and the upper die support member 102 is formed with a projection 102*a* projecting downward from an underside in a middle between left and right ends thereof in FIG. 8A. The upper die support member 102 and the lower die support member 101 are rotatably supported about the horizontal pin 100 (i.e., set to an opened and closed state) in a state that the horizontal pin 100 is horizontally fitted in a hollow of the projections 101*a* and 102*a*.

One end (in FIG. 8A, right end) of the lower die support member 101 is connected to a corresponding one of the upper die support member 102 via a tension spring 104. A cam 106 is interposed in a proximity between one end of the lower die support member 101 and the corresponding one of the upper die support member 102, and is connected to an output shaft 110 of a cam drive motor 108. The cam 106 is configured such that the lower and upper die support members 101 and 102 are pivotally moved in accordance with a rotation of the cam 106 by the cam drive motor 108.

Figure 8B:
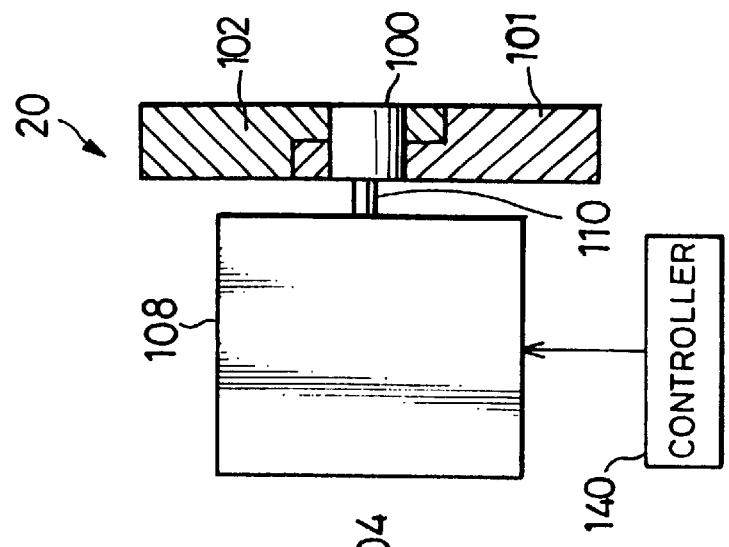
FIG. 8B is a cross-sectional view of the needle swaging device taken along the line 8B—8B in FIG. 8A.
Figure 8A:
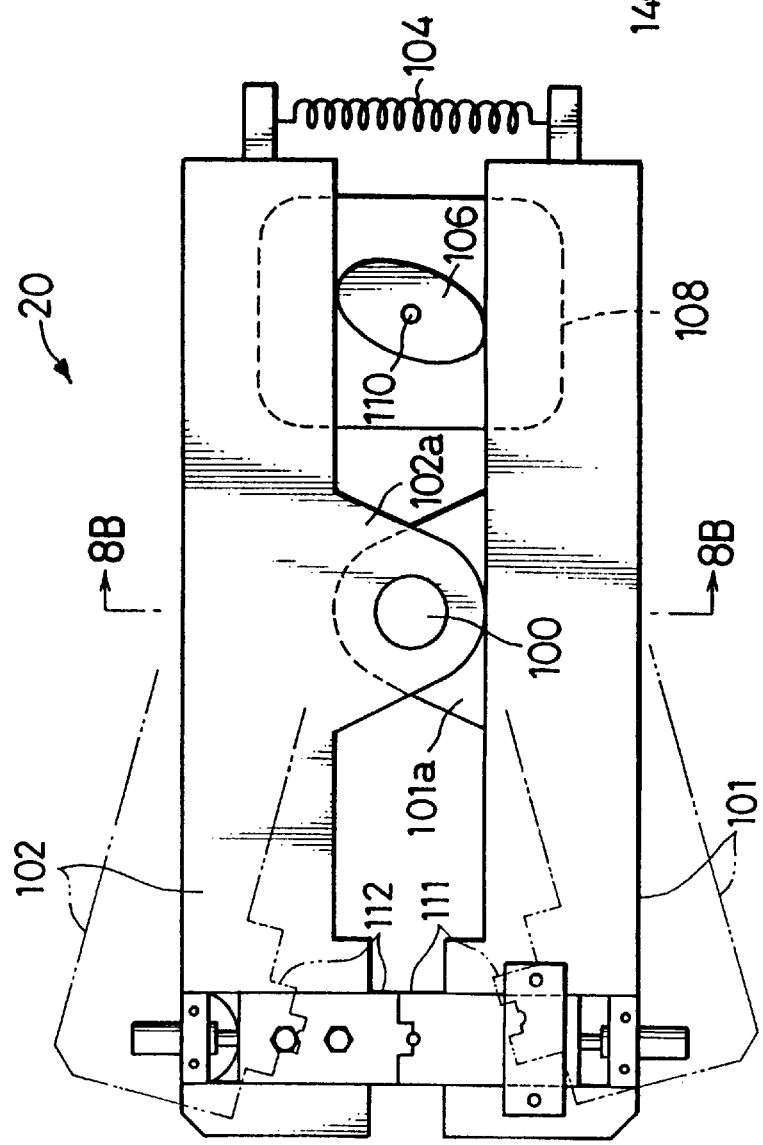
FIG. 8A is a front view of the needle swaging device.
Figure 9:
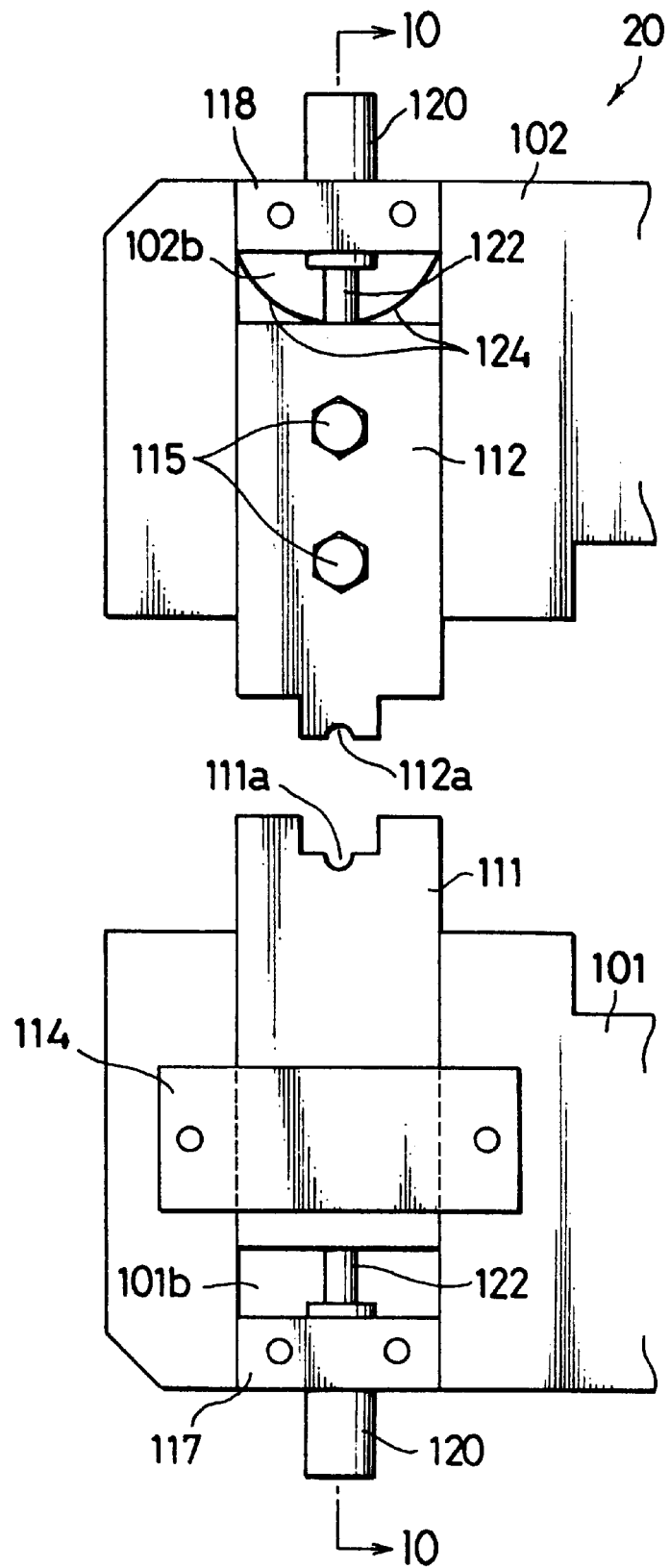
FIG. 9 is a front view showing an essential portion of the needle swaging device.
Figure 10:
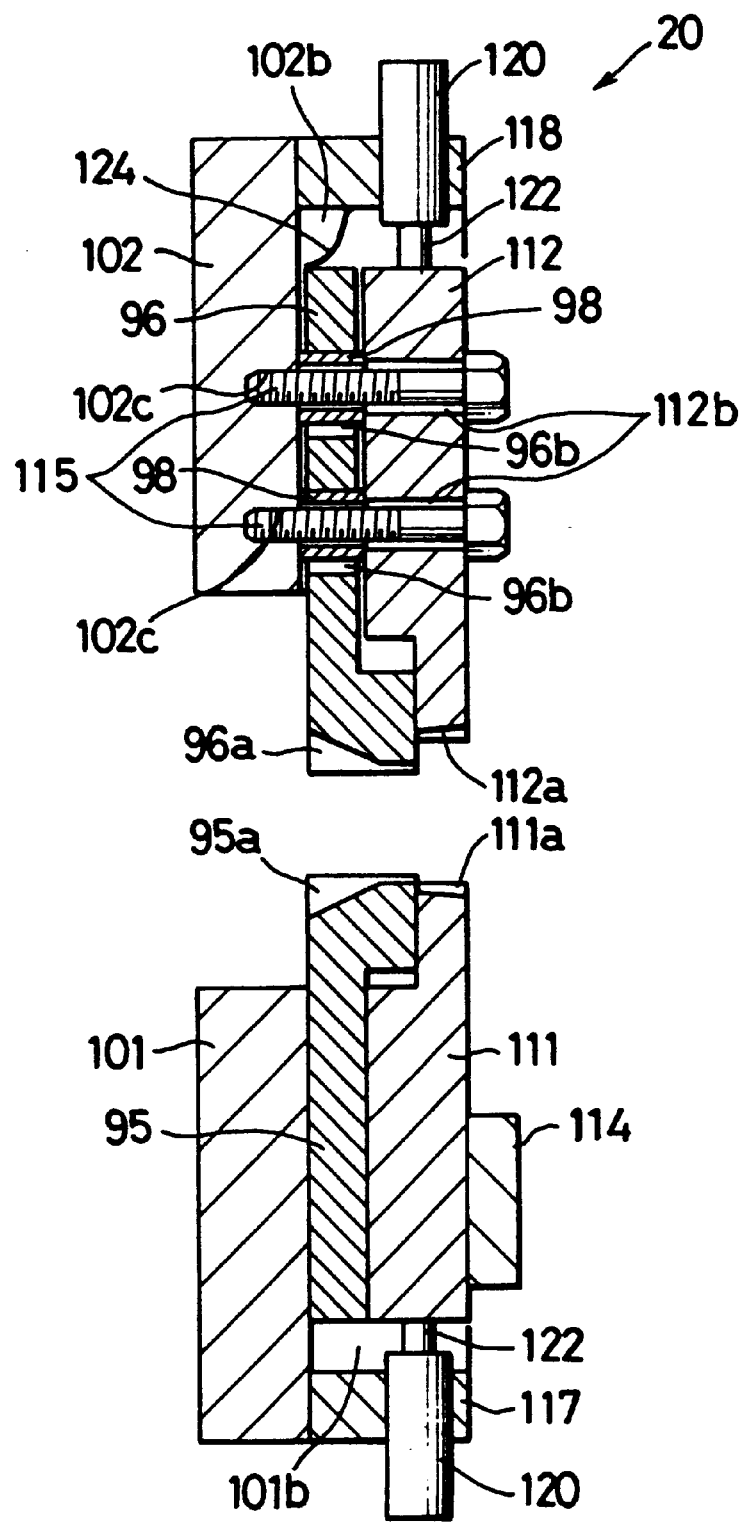
FIG. 10 is a cross-sectional view of the needle swaging device taken along the line 10—10 in FIG. 9.

At the opposite end (left end portion in FIG. 8A) of the lower die support member 101, as shown in FIGS. 9 and 10, there are mounted a lower swaging die 111 and a suture guide plate 95 (a divided half of suture guide means). At the opposite end of the upper die support member 102, there are mounted an upper swaging die 112 and a suture guide plate 96 (divided other half of the suture guide means).

As shown in FIGS. 9 and 10, a recess 111*a* in the form of a semi-circle having a radius smaller than that of the end of the needle N is formed in a middle of an upper end of the lower swaging die 111. A tapered (funnel-like shape or semi-conical shape) suture guide groove 95*a* is formed at a upper end of the suture guide plate 95 with the size (radius) thereof decreased toward the lower swaging die 111. The outlet radius of the suture guide groove 95*a* is set slightly larger than that of a suture insertion hole 116 of the needle N shown in FIG. 12.

A die fitting hollow 101*b* is formed in a side of the lower die support member 101 extending vertically with a width identical to the lower swaging die 111 and the suture guide plate 95. The suture guide plate 95 and the lower swaging die 111 are fitted in the die fitting hollow 101*b* and clamped on the lower die support member 101 by clamp means via a fixing plate 114 (i.e., the displacement in the widthwise direction of the suture guide plate 95 and the lower swaging die 111 is restricted).

Figure 11:
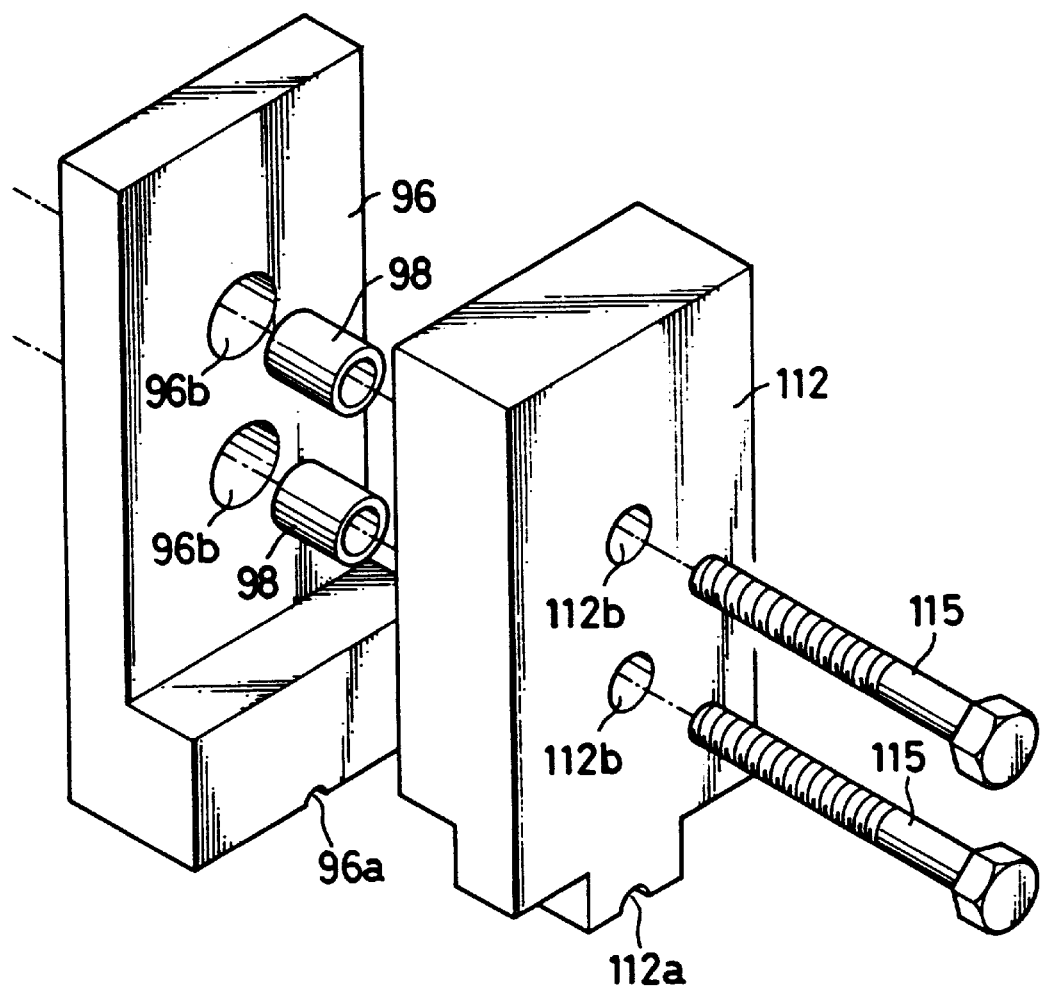
FIG. 11 is an exploded perspective view showing how an upper swaging die and a suture guide plate are assembled in the needle swaging device.

As shown in FIG. 11, a recess 112*a* in the form of a semi-circle with a radius smaller than the radius of the end of the needle N is formed in a middle of a lower end of the upper swaging die 112, i.e., at a position opposing to the semi-circular recess 111*a* of the lower swaging die 111. There are formed bolt insertion holes 112*b* (in the drawing, two holes are shown) in the middle of the upper swaging die 112.

A tapered (funnel-like shape or semi-conical shape) suture guide groove 96*a* is formed in a lower end of the suture guide plate 96 with the size (radius) thereof decreased toward the upper swaging die 112. The outlet radius of the suture guide groove 96*a* is set slightly larger than the suture insertion hole 116 of the needle N shown in FIG. 12. A spacer insertion hole 96*b* is formed in the suture guide plate 96 at a position corresponding to a bolt insertion hole 112*b* of the upper swaging die 112 with a diameter sufficiently greater than the bolt insertion hole 112*b*. A tubular spacer (boss) 98 is inserted in the spacer insertion hole 96*b*. An outer diameter of each spacer 98 is set smaller than the spacer insertion hole 96*b*, and an inner diameter thereof is set substantially the same as the diameter of the bolt insertion hole 112*b*. An axial length of the spacer 98 is slightly greater than a thickness of the suture guide plate 96.

A die fitting hollow 102*b* is formed in a side of the upper die support member 102 extending vertically with a width identical to the upper swaging die 112 and the suture guide plate 96. The suture guide plate 96 and the upper swaging die 112 are fitted in the die fitting hollow 102*b* (i.e., displacement in the widthwise direction of the suture guide plate 96 and the upper swaging die 112 is restricted), a die fixing bolt 115 is inserted in the bolt insertion hole 112*b* and in the spacer 98, and the end of the die fixing bolt 115 is fitted in a screw hole 102*c* (see FIG. 10) formed in the upper die support member 102 and engaged therewith. Thus, the upper swaging die 112 and the suture guide plate 96 are fixedly mounted on the upper die support member 102. The diameter of the die fixing bolt 115 is set smaller than the diameter of the bolt insertion hole 112*b* and the inner diameter of the spacer 98.

In this way, the suture guide plate 96 is vertically movable relative to the upper die support member 102 to set a dimension corresponding to a gap between the diameter of the spacer insertion hole 96*b* and the outer diameter of the spacer 98.

A mounting block 117 is fixed on the lower end of the die fitting hollow 101*b* of the lower die support member 101. A micrometer 120 is fixed on the mounting block 117 in an upright posture through the mounting block 117 (i.e., in a state that a lead end 122 of the micrometer 120 is directed upward).

Similarly, a mounting block 118 is fixedly mounted on the upper end of the die fitting hollow 102*b* of the upper die support member 102. A micrometer 120 is fixed on the mounting block 118 in an upright posture through the mounting block 118 (i.e., in a state that a lead end 122 of the micrometer 120 is directed downward).

Each micrometer 120 is operated such that the lead end 122 is axially moved a small amount in accordance with a rotation of the base end thereof (opposite to the lead end 122) to thereby push the lower and upper swaging dies 111 and 112 in a needle swaging direction. In this way, a state that the swaging dies 111 and 112 are pressed to each other is maintained in contact with the respective lead ends 122 and 122 of the micrometers 120 and 120.

An elastic wire 124 (bias means) having an arch shape is mounted on a lower side of the mounting block 118 of the upper die support member 102 in such a manner that a lead end thereof is fixedly connected to the lower side of the mounting block 118. The suture guide plate 96 is moved up and down with an elastic deformation of the wire 124. Further, the suture guide plate 96 is biased downward by a biasing force of the wire 124.

The positional relationship of the suture guide plate 95 relative to the lower swaging die 111 is set such that the upper surface of the suture guide plate 95 slightly projects upward from the upper surface of the lower swaging die 111. On the other hand, the positional relationship of the suture guide plate 96 relative to the upper swaging die 112 is set such that the lower surface of the suture guide plate 96 projects downward from the lower surface of the upper swaging die 112 greatly when the suture guide plate 96 is located at a lowermost position (i.e., the upper circumferential surface of the spacer 98 comes into contact with the upper circumferential surface of the spacer insertion hole 96b as shown in FIG. 10).

A controller 140, such as a microcomputer, is connected to the cam drive motor 108. The controller 140 sequentially controls operations of the various elements of the apparatus, including the cam drive motor 108. The control operations of the controller 140 are described later in detail.

Figure 13:
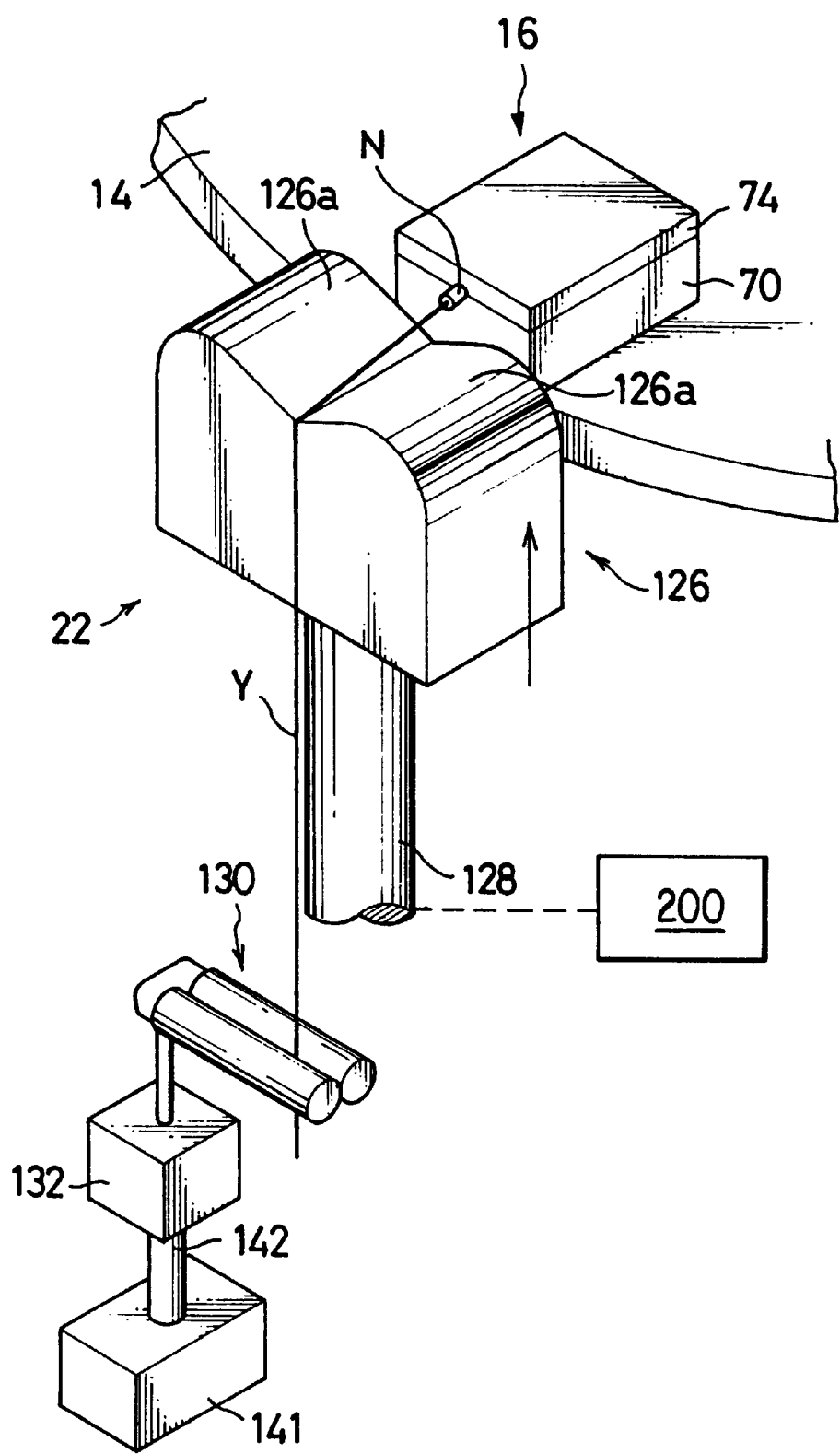
FIG. 13 is a perspective view of an arrangement of a pull test device in the manufacturing apparatus.

The detailed arrangement of the pull test device 22 is described with reference to FIG. 13. The pull test device 22 has a movable block (suture manipulator means) 126, and a clip (weight link means) 130. The clip 130 is connected to a weight member 132 having a weight corresponding to the minimum required pull out force of the suture Y with which the suture Y may be pulled out from the needle N. When the clip 130 clips the suture Y swaged in the needle N which is retained by the needle retaining unit 16, the suture Y is linked to the weight member 132.

The movable block 126 has an upper surface formed with a V-shape recess for guiding the suture Y therealong, and is fixed to an upper end of a shaft 128 which is coupled to an elevator mechanism 200. First, the elevator mechanism 200 is driven to move the movable block 126 upward to render the upper surface of the movable block 126 substantially flush with the suture Y and the needle combination, and maintains its level. In this state, the suture Y is linked to the weight member 132 which is supported on the lead end of an extendable rod 142 of an air cylinder (weight release means) 141. Subsequently, the extendable rod 142 is contracted at a sufficiently low speed to gradually move downward away from the weight member 132.

It should be noted that "sufficiently low speed" in this description means that the extendable rod 142 is contracted at such a speed as not to give a dynamic load (impact force or vibration force exceeding the stationary load corresponding to the weight of the weight member 132) to the suture Y when the upper surface of the extendable rod 142 is lowered away from the weight member 132 to set the weight member 132 in a hung state.

An operation of the needle attached suture manufacturing apparatus according to the invention is described below.

Referring to FIG. 1, the needle N supplied to the predetermined position on the needle supply device 2 is transported to the predetermined position on the adjuster table 8 of the needle orientation adjuster device 6 by the needle transport device 4, and is placed thereat.

The image recognizer 10 recognizes an image of the needle N placed on the adjuster table 8, and the adjuster table 8 is moved in the respective directions so as to coincide the direction and the position of the recognized image, with those of the target image which is stored in advance. Thereafter, the needle N is picked up by the needle pickup device 12 and carried to the needle retaining unit 16 on the turntable 14.

When the needle is about to be carried to the needle retaining unit 16, the air cylinder 76 shown in FIG. 2 is expanded to push up the openable plate 74, thereby exposing the upper surface of the retainer main body 70 outside. Then, the needle N is placed on the retainer main body 70 in a state that the end of the needle N is jutted outward from the retainer main body 70. Thereafter, the air cylinder 76 is contracted to close the openable plate 74 by the weight thereof, thereby allowing the needle N to be retained by the needle retaining unit 16. In this state, the turntable 14 is rotated to a specified angular position. Thereby, the needle retaining unit 16 carrying the needle N is transported to the needle end adjuster device 18, where the end of the needle N is pushed to a certain position to finely position the end of the needle. Thereafter, the turntable 14 is angularly displaced to transport the needle retaining unit 16 carrying the needle N to the needle swaging device 20.

Figure 12A:
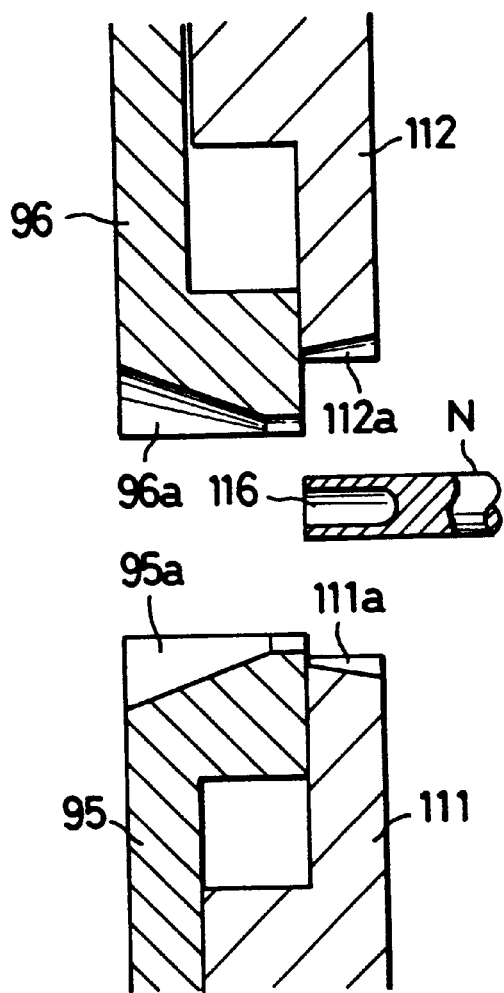
FIG. 12A is a cross-sectional side view showing a state in which the upper swaging die and a lower swaging die are spaced away from the end of the needle a sufficient distance.

When the needle N is carried to the needle swaging device 20, as shown by the phantom line in FIG. 8A and FIG. 12A, the upper swaging die 112 and the lower swaging die 111 are opened up away from each other to define a large opening. In this state, the turntable 14 is rotated to a certain angular position to transport the end of the needle N in the opening between the upper swaging die 112 and the lower swaging dies 111.

In the meantime, the suture supply device 28 shown in FIG. 3 conducts the following steps of cutting the suture Y and inserting the lead end of the suture in the suture insertion hole 116 of the end of the needle N.

1) The holding means 32 and 38 hold the suture Y. The tension supplier 33 is actuated to supply a certain tension force to the suture Y between the holding means 32 and 38.

Figure 4A:
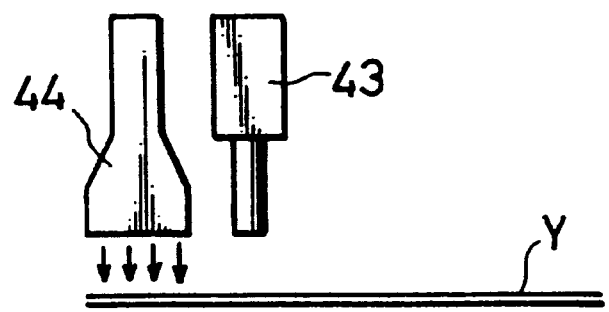
FIGS. 4A to 4D are front views showing a series of curing agent application operations conducted by a curing agent nozzle.
Figure 4B:
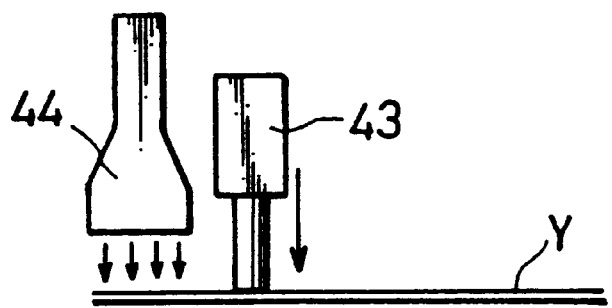
Figure 4C:
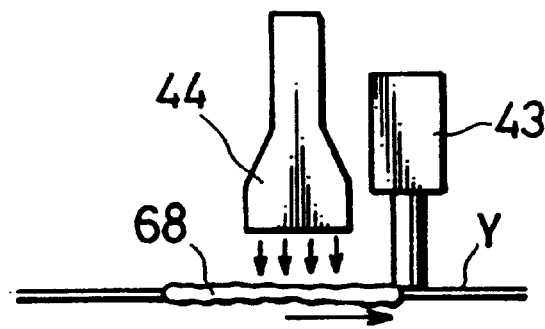
Figure 4D:
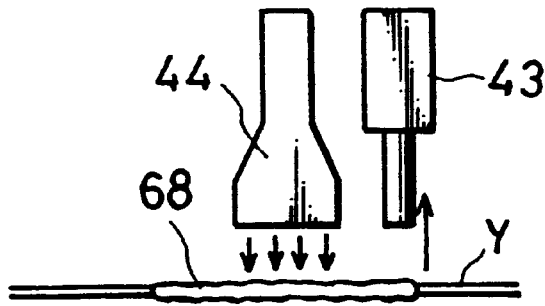

2) The curing agent nozzle 43 and the dryer 44 shown in FIG. 4 are moved as a one-piece unit to a position just above the suture Y (see FIG. 4A). Subsequently, the curing agent nozzle 43 is lowered to render the lead end of the nozzle 43 in contact with the suture Y (see FIG. 4B). Thereupon, an air cylinder (not shown) expandable and contractible in a direction parallel to the suture feed direction is expanded to transport the curing agent nozzle 43 and the dryer 44 toward a predetermined cutting position by the cutter 37 (see FIG. 4C).

During conveyance of the nozzle 43 and the dryer 44, a curing agent 68 supplied from the nozzle 43 is coated on the surface of the suture Y, while the dryer 44 blowing heated air onto the coated surface of the suture Y follows the nozzle 43. Curing of the curing agent 68 is thereby accelerated.

3) Subsequently, the nipping device pair 36 nips the suture Y, and the cutter 37 cuts the suture Y at the predetermined the cutting position. At the same time of cutting operation, the nipping devices 32 and 38 release holding of the suture Y.

4) At this time, the transport/holding device 42 is located at the position between the nipping device pair 36 at which the suture Y is nipped. At this time, the lead end position of the suture Y corresponds to the cutting position by the cutter 37 in the previous cutting operation. Accordingly, the transport/holding device 42 holds a portion near the lead end of the suture Y. Note that, at this time, the lead end of the suture Y has already been stiffened with the curing agent 68.

5) After the nipping device pair 36 releases holding of the suture Y, the rodless cylinder 46 is activated to transport the transport/holding device 42 linearly straight toward the needle N (which is held by the needle retaining unit 16). Upon confirming that the transport/holding device 42 travels a distance corresponding to a length at which the suture is to be cut, operation of the rodless cylinder 46 is suspended, thereby halting the transport/holding device 42 thereat. In this way, the above operations 1) to 5) are repeated a certain number of times to obtain suture strands exactly cut with the predetermined target length (=L).

After the transport/holding device 42 feeds the suture Y the predetermined distance, and the cutter 37 cuts the suture Y at the cutting position, the center positioning/nipping device 40 is set to the nipping position to thereby position the center of the lead end of the suture. Subsequently, the insertion/nipping device 39 holds the suture Y. Then, the transport/holding device 42 releases the suture Y, and returns to the initial position between the nipping device pair 36 (position shown in the step 4)). Upon returning of the transport/holding device 42 to the initial position, the center positioning/nipping device 40 releases the suture Y and then moves to the retracted position below the suture Y.

Referring to the needle swaging device 20 which id under the control of the controller 140, the upper die support member 102 and the lower die support member 101 are moved toward a pre-swaging position with a rotation of the cam 106 to render the upper swaging die 112 and the lower swaging die 111 closer to each other.

Figure 12B:
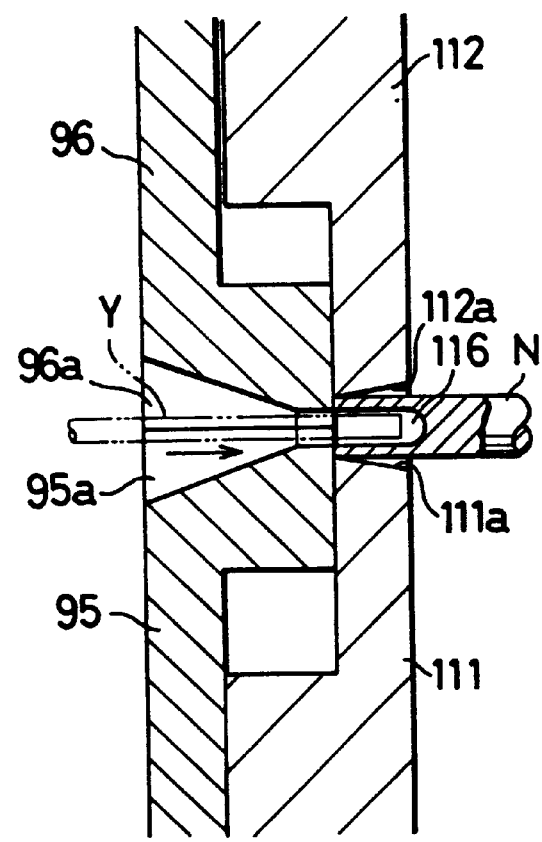
FIG. 12B is a cross-sectional side view showing a state in which the upper and lower swaging dies are set at a pre-swaging position.

The "pre-swaging position" is a position before the swaging position. As shown in FIG. 12B, the pre-swaging position is set such that the recess 111a of the lower swaging die 111 and the recess 112a of the upper swaging die 112 touch the outer circumference of the end of the needle N (i.e., a state that the touch is insignificant enough not to cause deformation of the end of the needle), or come in close proximity with the end thereof.

It should be noted that the lower surface of the suture guide plate 96 is set lower than the lower surface of the upper swaging die 112 more significantly, as mentioned above (see FIG. 12A), before the swaging dies 111 and 112 are set to the pre-swaging position. Accordingly, in the course of movement of the swaging dies 111 and 112 toward the pre-swaging position, the suture guide plates 95 and 96 come into contact with each other before the swaging dies 111 and 112 reach the pre-swaging position. Upon coming into contact with the suture guide plate 95, the lowering movement of the suture guide plate 96 is stopped. At this state, the upper die support member 102 and the upper swaging die 112 are still further lowered and pressed against an elastic restoring force of the wire 124. Thus, the upper swaging die 112 (the upper die support member 102) reaches the pre-swaging position.

Figure 7:
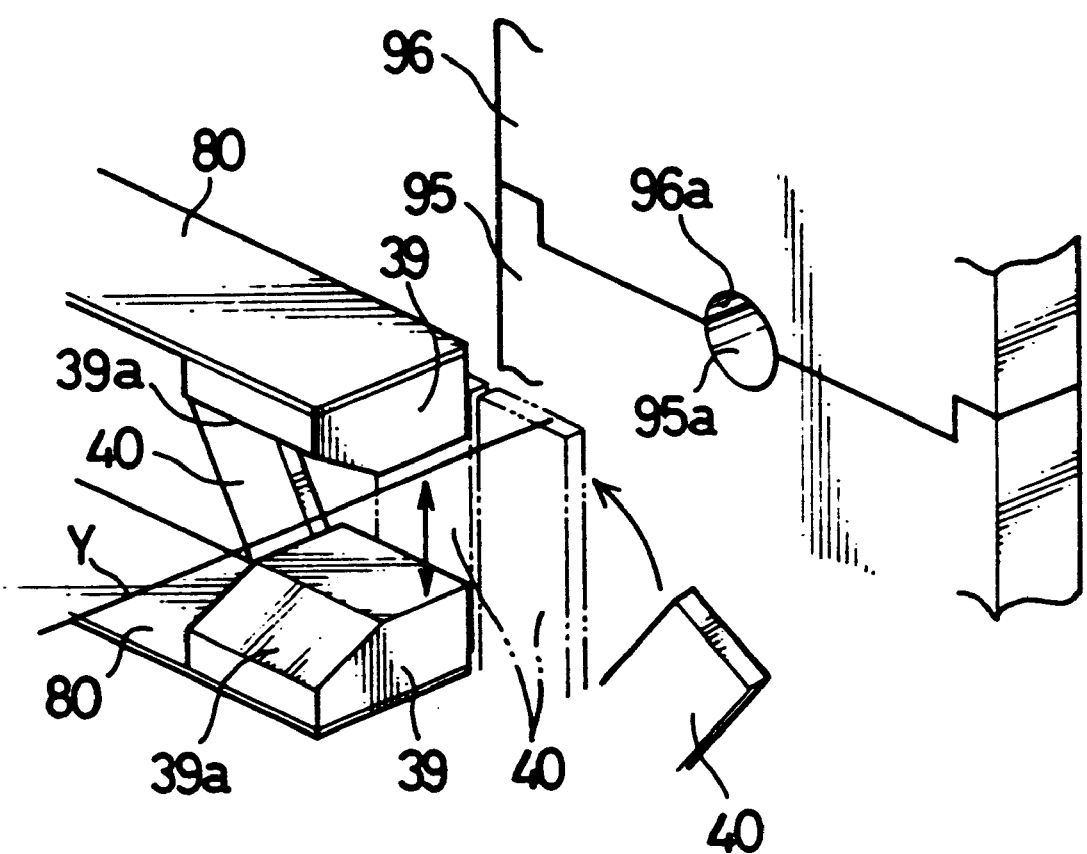
FIG. 7 is a partially cross-sectional perspective view showing a positional relationship between the insertion/nipping device, center positioning/nipping device, and a needle swaging device.

When the lower and upper swaging dies 111 and 112 are set to the pre-swaging position, the suture guide groove 95a of the suture guide plate 95 and the suture guide groove 96a of the suture guide plate 96 are jointed each other to define a funnel-like (conical) suture guide hole as a whole shape. As shown in FIG. 7, the suture guide hole is opened up toward the insertion/nipping device 39.

In this state, when the insertion/nipping device 39 holding the suture Y moves toward the suture guide plates 95 and 96, the lead end of the suture Y is smoothly and securely inserted into the insertion hole 116 of the end of the needle N which is retained by the needle retaining unit 16 via the suture guide hole (see the phantom line in FIG. 12B).

Note that the insertion operation is conducted after the cutting operation of the suture Y.

After the insertion, the swaging dies 111 and 112 come closer to each other to press the end of the needle N vertically. Thus, the end of the needle is swaged with a certain swaging force to fixedly attach the lead end of the suture to the needle N. After the swaging, the swaging dies 111 and 112 are moved away from each other to release the needle N, and the turntable 14 is raised a small amount and angularly displaced to transport the needle N to the pull test device 22 to inspect whether the swaging force is sufficient.

Specifically, the movable block 126 is raised from the lowermost position to lift an intermediate portion of the suture Y which is drooped down from the needle N held by the needle retaining unit 16. When the intermediate portion of the suture Y is raised to a level substantially flush with the combined portion of the needle and the suture, the movement of the movable block 126 is suspended to support the suture Y thereat.

Subsequently, the clip 130 clips the suture Y in a state that the weight member 132 is placed on the upper surface of the extendable rod 142 of the air cylinder 141. Thus, the suture Y is linked to the weight member 132 via the clip 130. In this state, the extendable rod 142 of the air cylinder 141 gradually contracts to move slowly downward away from the weight member 132, thereby setting the weight member 132 in a hung state. With this operation, a stationary load corresponding to the weight of the weight member 132 is loaded on the suture Y. During the tensile test of loading the stationary load, when the suture is pulled out from the needle N, such needle attached suture is judged "unacceptable" because of an insufficient swaging force, whereas the needle attached suture is judged "acceptable" when the suture Y safely stays in the needle N.

After inspection by the pull test device 22, the turntable 14 is angularly displaced to a predetermined position for pickup operation by the needle discharge device 24 in a state that the needle retaining unit 16 carries the needle N with the suture attached thereto. At this time, the acceptable needles (i.e., needle with the suture securely attached thereto) are discharged on the needle discharge table 26 by the needle discharge device 24, while unacceptable needles (i.e., needle without the suture, which is pulled out therefrom) are transferred to a position different from the needle discharge table 26 by the needle discharge device 24.

As mentioned above, the manufacturing apparatus according to this invention is constructed such that: the suture guide means consists of a pair of suture guide plates 95 and 96; and these suture guide plates 95 and 96 are respectively mounted on the die support members 101 and 102 to open and close the suture guide plates 95 and 96 and along with the swaging dies 111 and 112. Accordingly, compared to the conventional apparatus in which the suture guide means is provided independently of the swaging dies 111 and 112, the arrangement of the present invention attains positioning of the suture guide means (suture guides plates 95 and 96) relative to the suture insertion hole 116 with high precision. Thus, the suture guide plates 95 and 96 provide accurate and smooth insertion of the suture Y into the insertion hole 116 of the needle.

The present invention is not limited to the aforementioned embodiment, and may incorporate the following modifications and alterations.

(1) The arrangement of the swaging drive means is not limited to the combination of the cam 106 and the cam drive motor 108. An air cylinder may be used to move the swaging dies 111 and 112 toward and away from each other. However, the arrangement that the cam 106 is interposed between the die support members 101 and 102 can finely adjust the position of the swaging dies 111 and 112, and hence, the pre-swaging position and the swaging position can be adjusted minutely according to needs even if the diameter of the needle N is varied.

(2) According to this invention, even if the suture guide plates 95 and 96 are fixed on the die support members 101 and 102 to restrict a movement of the suture guide plates relative to the die support members, guiding of the suture into the insertion hole of the needle and a swaging operation that follows can be performed. In this case, however, if the suture guide plates 95 and 96 have already come into contact with each other when the swaging dies 111 and 112 are moved to the pre-swaging position, the die support members 101 and 102 cannot move closer to each other anymore, resulting in an incapability of performing a swaging operation that follows. Accordingly, in order to avoid such drawback it is required to set the position of the suture guide plates 95 and 96 in such a manner that there is left a small clearance between the suture guide plates 95 and 96 (i.e., a state that the suture guide plates come in close contact to each other) when the swaging dies 111 and 112 are set to the pre-swaging position. However, this arrangement may likely cause a drawback that the lead end of the suture is trapped in the small clearance between the suture guide plates 95 and 96 in the course of inserting the lead end of the suture into the insertion hole of the needle.

The arrangement of the aforementioned embodiment in which the suture guide plate 96 is (vertically) adjustable relative to the upper die support member 102 by the bias means such as the wire 124 is advantageous in the following point. There is allowed a further positioning of the suture guide plate 96 to the suture guide plate 95 utilizing a bias force of the bias means to more accurately guide the insertion of the suture into the insertion hole of the needle because the suture guide plates 95 and 96 should come into contact with each other when the swaging dies 111 and 112 are set to the pre-swaging position. This secures a precise swaging operation after the insertion step.

The same effect is obtainable by the arrangement in which the suture guide plate 95 is provided on the lower die support member 111 while allowing relative displacement from each other.

(3) The micrometer 120 may be omitted. However, the use of micrometer is advantageous in accurately positioning the swaging dies 111 and 112 against a reaction force resulting from a swaging operation.

(4) The center positioning/nipping device 40 may vertically nip the suture Y, similar to the insertion/nipping device 39. In this case, also, the lead end of the suture Y can be accurately inserted in the insertion hole of the needle. However, holding of the suture by the insertion/holding device 39 can adjust the position of the suture Y in the holding direction (in the drawing, vertical direction) to a certain extent. Accordingly, the arrangement of the center positioning/nipping device 40 to nip the suture Y in a direction orthogonal to the suture holding direction of the insertion/nipping device 39 (in the drawing, front and rear directions) is advantageous in aligning the lead end of the suture Y with the insertion hole of the needle more accurately.

(5) In the above embodiment, the suture guide plates 95 and 96 are directly mounted on the die support members 101 and 102, respectively. Alternatively, the suture guide plates 95 and 96 may be mounted on the die support members 101 and 102 via the swaging dies 111 and 112 by fixedly mounting the suture guide plates 95 and 96 on a side of the swaging dies 111 and 112 using fixing means such as bolt.

(6) In the foregoing embodiment, the extendable rod 142 slowly contracts and lowers away from the weight member 132 from a support state where the weight member 132 is supported on the extendable rod 142 to load a stationary load on the suture Y. In place of this arrangement, the weight member 132 (linked to the suture Y) is placed on abase member, and then the movable block 126 is slowly raised from the initial lowermost position to lift up the intermediate portion of the suture. Thus, the weight member 132 is slowly set to a hung state above the base member, thereby loading a stationary load to the suture Y.

(7) The arrangement of the insertion means is not limited to the one shown in the above embodiment. For example, insertion/nipping devices 150A and 150B shown in FIGS. 14 and 15 may be used.

Figure 14:
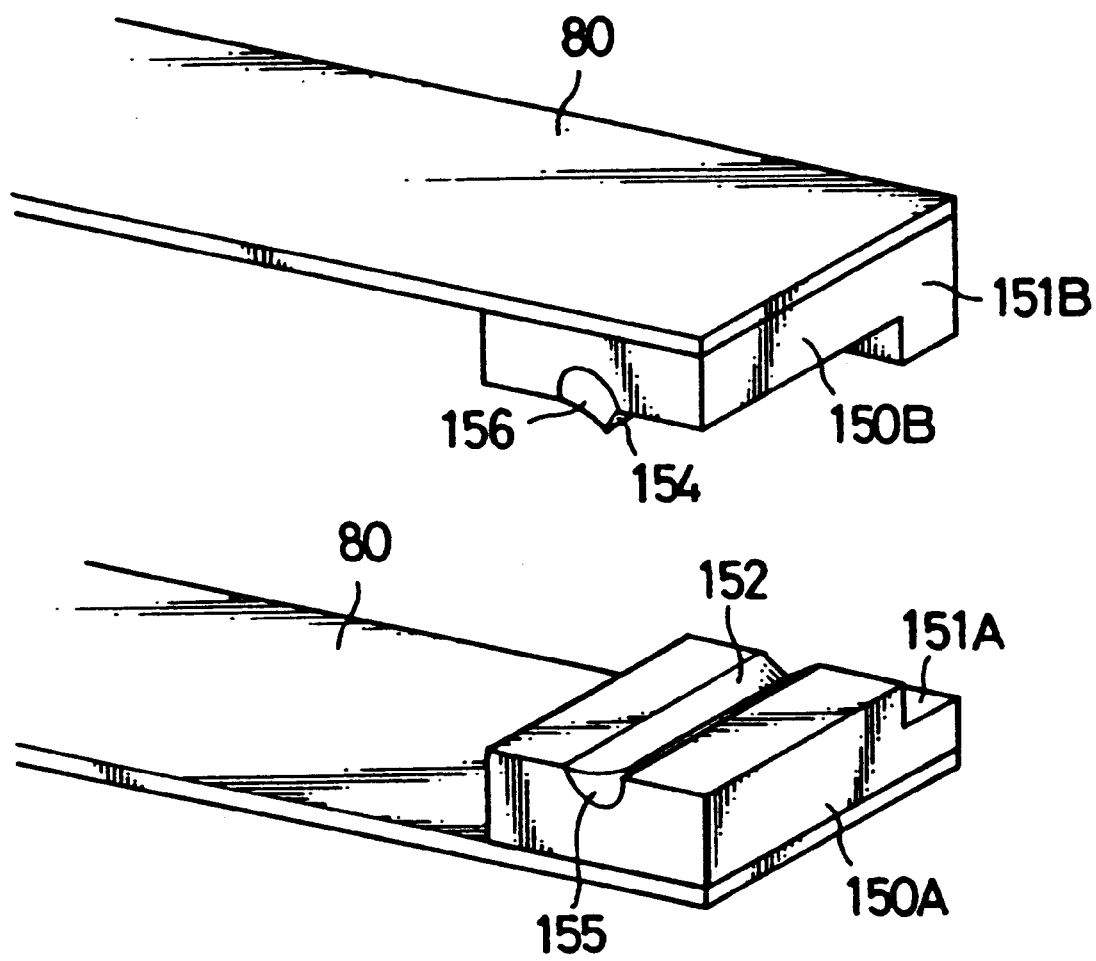
FIG. 14 is a perspective view showing a modification of the insertion/nipping device of this invention.
Figure 15:
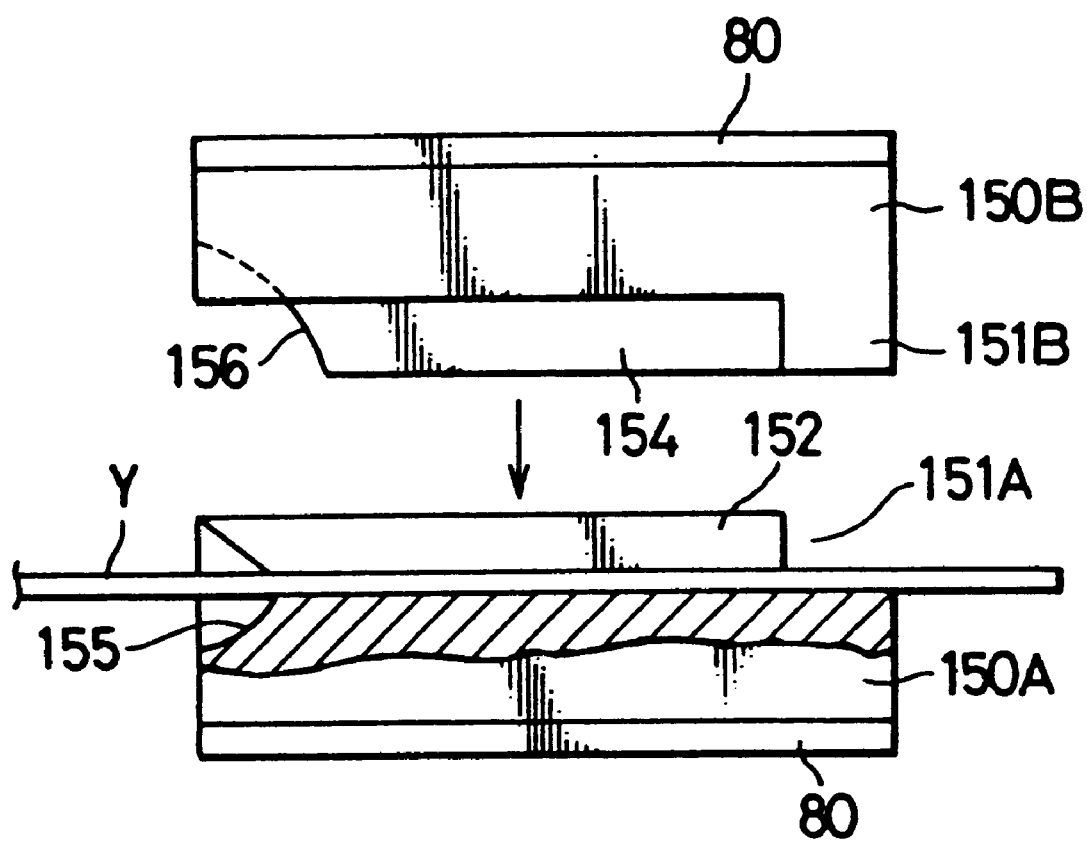
FIG. 15 is a partially cross-sectional side view of the insertion/nipping device of FIG. 14.

In FIGS. 14 and 15, the lower insertion/nipping device 150A is formed with a V-shaped groove 152 extending in the suture insertion direction, while the upper insertion/nipping device 150B is formed with a ridge 154 projecting downward at the position corresponding to the V-shaped groove 152. Tapered guide portions 155 and 156 are formed on the suture inlet side (left side in FIG. 15) of the insertion/nipping devices 150A and 150B respectively to guide the lead end of the suture. A stepped portion 151A with the same depth as the V-shaped groove 152 is formed on the suture outlet side (right side in FIG. 15) of the lower insertion/nipping device 150A. A projection wall 151B projecting downward with the same height as the ridge 154 is formed on the suture outlet side of the upper insertion/nipping device 150B.

According to the arrangement of the insertion/nipping devices 150A and 150B, the suture Y can be held accurately at the center position of the V-shaped groove 152 (at the bottom end). Further, the tapered guide portions 155 and 156 can smoothly guide the insertion of the lead end of the suture Y to the insertion/nipping devices 150A and 150B.

EXPLOITATION IN INDUSTRY

As mentioned above, the present invention is effectively applicable, in the field of producing needle attached sutures, to an apparatus for attaching a suture to the end of a surgical needle or its equivalent.

We claim:

1. An apparatus for manufacturing a needle attached suture in which an end of a needle is swaged with a lead end of a suture inserted in an insertion hole formed in the end of the needle to combine the suture with the needle, the apparatus comprising:

needle retaining means for holding the needle with at least the end thereof protruding from the needle retaining means;

insertion means for inserting the lead end of the suture into the insertion hole of the needle held by the needle retaining means by transporting the lead end in a suture insertion direction;

swaging dies for swaging the end of the needle at a swaging position by moving from substantially opposing swaging directions to swage the end of the needle with the suture inserted in the insertion hole of the needle to fix the suture in the insertion hole;

die support members for respectively supporting the swaging dies, said die support members having said swaging dies respectively mounted thereon and said die support members being moveably coupled together to permit movement of said die support members relative each other in said opposing swaging directions;

swaging drive means for moving the die support members relatively toward and away from each other along the substantially opposing swaging directions to move the die support members and the swaging dies between a pre-swaging die position whereat the swaging dies are positioned in one of contact or close proximity with the end of the needle which is in an unswaged state and a swaging position whereat the swaging dies are positioned to swage the end of the needle;

suture guide members provided between the insertion means and the swaging dies, the suture guide members each having a concavity configured and disposed so as to form a tapered guide hole when the suture guide members are brought in contact with each other, the tapered guide hole having a diameter decreasing along the suture insertion direction toward the insertion hole of the needle; and the suture guide members being mounted on respective ones of the die support members such that the suture guide members are positioned in one of in contact or in close proximity with each other when the die support members are at the pre-swaging position.

2. The apparatus according to claim 1, further comprising swaging control means for controlling the swaging drive means to position the die support members at a first position apart from one another, at the pre-swaging position before the end of the needle is swaged and at the swaging position whereat the end of the needle is swaged.

3. The apparatus according to claim 1, wherein:
at least one of the suture guide members is movably disposed on the die support member to be movable relative to the die support member in a direction substantially parallel with the needle swaging direction; and
biasing means are provided to bias the at least one of the suture guide members toward another one of the suture guide members, and the suture guide members are set to come into contact with each other when the die support are relatively positioned to the pre-swaging position.

4. The apparatus according to claim 3, wherein a position of at least one of the swaging dies is adjustable with respect to a respective one of the die support members upon which it is supported in the needle swaging direction.

5. The apparatus according to claim 1, further comprising a die position adjustment mechanism for adjusting a position at which at least one adjustable swaging die of the swaging dies is disposed with respect to a respective one of the die support members upon which it is supported, the adjustable swaging die being adjustable in the needle swaging direction.

6. The apparatus according to claim 5, wherein the die position adjustment mechanism includes the respective one of the die support members defining a groove extending in the needle swaging direction in which the adjustable swaging die is fitted to restrict a displacement of the adjustable swaging die in a direction orthogonal to the needle swaging direction and permit displacement in the needle swaging direction.

7. The apparatus according to claim 6, wherein the die support member is provided with a positioning means for moving the adjustable swaging die in the needle swaging direction a known amount proportional to adjustment of the positioning means.

8. The apparatus according to claim 7, wherein said positioning means is a micrometer.

9. The apparatus according to claim 5, wherein the die position adjustment mechanism includes:
the adjustable swaging die defining a bolt insertion hole having a bolt insertion hole diameter;
a corresponding suture guide member of the suture guide members defining a spacer insertion hole at a position corresponding to the bolt insertion hole and having a spacer insertion hole diameter;
a tubular spacer having a spacer inner diameter, a spacer outer diameter smaller than the spacer insertion hole diameter and a spacer axial length greater than a guide member thickness of the corresponding suture guide member;
the tubular spacer being disposed in the spacer insertion hole whereby the spacer outer diameter being smaller than the spacer insertion hole diameter permits the suture guide member to be movable with respect to the tubular spacer disposed within the spacer insertion hole;
a die fixing bolt inserted in the bolt insertion hole of the adjustable swaging die and in the tubular spacer disposed in the spacer insertion hole of the corresponding suture guide member;
the die fixing bolt having a bolt diameter smaller than the spacer inner diameter and the bolt insertion hole diameter; and
the die fixing bolt being engagable with the respective one of the die support members to fix the tubular spacer and the adjustable swaging die on the die support member while permitting movement of the corresponding suture guide member when the die fixing bolt is in a tightened state and to permit positional adjustment of the adjustable swaging die when in a loosened state.

10. The apparatus according to claim 9, wherein the die support member is provided with a positioning means for moving the adjustable swaging die in the needle swaging direction a known amount proportional to adjustment of the positioning means.

11. The apparatus according to claim 10, wherein said positioning means is a micrometer.

12. The apparatus according to claim 5, wherein the die support member is provided with a positioning means for moving the adjustable swaging die in the needle swaging direction an known amount proportional to adjustment of the positioning means.

13. The apparatus according to claim 12, wherein said positioning means is a micrometer.

14. The apparatus according to claim 1, wherein the insertion means holds a portion of the suture, other than the lead end, by clamping the suture between clamping members having clamping faces oriented in a clamping face direction, and transports the suture in the suture insertion direction toward the suture guide members to insert the lead end of the suture into the insertion hole at the end of the needle through the guide hole of the suture guide members.

15. The apparatus according to claim 7, further comprising aligning means provided between the insertion means and the suture members for nipping the lead end of the suture to align the position of the lead end of the suture with the insertion hole of the needle.

16. The apparatus according to claim 15, wherein the aligning means nips the lead end of the suture with nipping faces aligned in a nipping direction substantially orthogonal to the clamping face direction.

17. The apparatus according to claim 1, further comprising load supplier means for loading a specified stationary load on the suture combined with the needle in a state that the needle retaining means holds the needle while the specified stationary load is supported on the suture.

18. The apparatus according to claim 17, wherein the load supplier means includes:
   a weight member having a weight corresponding to the specified stationary load;
   the needle retaining means holding the needle with the needle end aligned in a horizontal direction;
   weight link means for linking the weight member to the suture while the suture hangs in a vertical direction;
   suture manipulator means for lifting an intermediate portion of the suture to a level substantially horizontal and aligned with a swaged portion of the suture and the needle; and
   weight release means for supporting the weight member when the weight link means initially links the weight member to the suture and for gradually removing support of the weight member to permit the specified stationary load of the weight member to be supported by the suture.

19. The apparatus according to claim 17, wherein the load supplier means includes:
   a weight member having a weight corresponding to the specified stationary load;
   the needle retaining means holding the needle with the needle end aligned in a horizontal direction;
   weight link means for linking the weight member to the suture in a state not supported by the suture while the suture hangs in a vertical direction; and
   suture manipulator means for setting the weight member from a supported state where the weight member is supported on a base member to a hung state by lifting an intermediate portion of the suture upward to gradually hang the weight member above the base member.

20. The apparatus according to claim 17, further comprising discharge means for transferring the suture combined with the needle to a specified discharge position after it is confirmed that loading the stationary load does not pull out the suture off the needle.

21. The apparatus according to claim 1, further comprising:
   a die position adjustment mechanism for adjusting a position at which at least one adjustable swaging die of the swaging dies is disposed with respect to a respective one of the die support members upon which it is supported, the adjustable swaging die being adjustable in the needle swaging direction;
   the die position adjustment mechanism including the respective one of the die support members defining a groove extending in the needle swaging direction in which the adjustable swaging die is fitted to restrict a displacement of the adjustable swaging die in a direction orthogonal to the needle swaging direction and permit displacement in the needle swaging direction;
   the die position adjustment mechanism including:
      the adjustable swaging die defining a bolt insertion hole having a bolt insertion hole diameter;
      a corresponding suture guide member of the suture guide members defining a spacer insertion hole at a position corresponding to the bolt insertion hole and having a spacer insertion hole diameter;
      a tubular spacer having a spacer inner diameter, a spacer outer diameter smaller than the spacer insertion hole diameter and a spacer axial length greater than a guide member thickness of the corresponding suture guide member;
      the tubular spacer being disposed in the spacer insertion hole whereby the spacer outer diameter being smaller than the spacer insertion hole diameter permits the suture guide member to be movable with respect to the tubular spacer disposed within the spacer insertion hole;
      a die fixing bolt inserted in the bolt insertion hole of the adjustable swaging die and in the tubular spacer disposed in the spacer insertion hole of the corresponding suture guide member;
      the die fixing bolt having a bolt diameter smaller than the spacer inner diameter and the bolt insertion hole diameter; and
      the die fixing bolt being engagable with the respective one of the die support members to fix the tubular spacer and the adjustable swaging die on the die support member while permitting movement of the corresponding suture guide member when the die fixing bolt is in a tightened state and to permit positional adjustment of the adjustable swaging die when in a loosened state.

22. The apparatus according to claim 21, wherein the die support member is provided with a positioning means for moving the adjustable swaging die in the needle swaging direction a known amount proportional to adjustment of the positioning means.

23. The apparatus according to claim 22, wherein said positioning means is a micrometer.

24. The apparatus according to claim 1, further comprising aligning means provided between the insertion means and the suture guide members for nipping the lead end of the suture to align the position of the lead end of the suture with the insertion hole of the needle.

25. The apparatus according to claim 24, wherein:
   the aligning means has nipping members with nipping faces oriented in a nipping face direction when nipping the lead end of the suture and said nipping face direction;
   the swaging dies have swaging faces brought together and oriented in a swaging face direction at the swaging position; and
   the nipping face direction is orthogonal to the swaging face direction.

26. The apparatus according to claim 25 wherein the aligning means includes means for pivoting at least one of said nipping members to engage a nipping face thereof with the nipping face of another of said nipping member to nip said lead end.

27. The apparatus according to claim 25 wherein the aligning means includes means for moving at least one of the nipping members moves horizontally right and left to nip the lead end.

28. The apparatus according to claim 24, wherein:
   the aligning means has nipping faces oriented in a nipping face direction when nipping the lead end of the suture and said nipping face direction;
   the suture guide members have the concavities disposed in guide faces which are brought together and oriented in a guide face direction at the preswaging position; and
   the nipping face direction is orthogonal to the guide face direction.

29. The apparatus according to claim 28 wherein the aligning means includes means for pivoting at least one of said nipping members to engage a nipping face thereof with the nipping face of another of said nipping member to nip said lead end.

30. The apparatus according to claim 28 wherein the aligning means includes means for moving at least one of the nipping members moves horizontally right and left to nip the lead end.

31. The apparatus according to claim 1, further comprising:

aligning means provided between the insertion means and the suture guide members for nipping the lead end of the suture to align the position of the lead end of the suture with the insertion hole of the needle;

the aligning means having nipping members with nipping faces oriented in a nipping face direction when nipping the lead end of the suture and said nipping face direction;

the aligning means including means for pivoting at least one of said nipping members to engage the nipping face thereof with the nipping face of another of said nipping members to nip said lead end.

32. The apparatus according to claim 31 wherein the aligning means includes means for moving at least one of the nipping members moves horizontally right and left to nip the lead end.

33. An apparatus for manufacturing a needle attached suture in which an end of a needle is swaged with a lead end of a suture inserted in an insertion hole formed in the end of the needle to combine the suture with the needle, the apparatus comprising:

needle retaining means for holding the needle with at least the end thereof protruding from the needle retaining means;

insertion means for inserting the lead end of the suture into the insertion hole of the needle held by the needle retaining means by transporting the lead end in a suture insertion direction;

swaging dies for swaging the end of the needle at a swaging position by moving from substantially opposing swaging directions to swage the end of the needle with the suture inserted in the insertion hole of the needle to fix the suture in the insertion hole;

die support members for respectively supporting the swaging dies, said die support members having first ends and second ends with said swaging dies respectively mounted proximate said first ends;

at least one of the die support members being mounted rotatable about an axis of rotation extending in a direction parallel to the suture insertion direction to permit relative movement of the die support members toward and away from each other, the axis of rotation being positioned between said first ends and said second ends of the die support members;

swaging drive means for moving the die support members relatively toward and away from each other along the substantially opposing swaging directions to move the die support members and the swaging dies between a pre-swaging die position whereat the swaging dies are positioned in one of contact or close proximity with the end of the needle which is in an unswaged state and a swaging position whereat the swaging dies are positioned to swage the end of the needle;

the swaging drive means including a cam interposed between the die support members at a position between the axis of rotation and the second ends of the die support members, and cam drive means for rotating the cam;

the cam being configured such that the swaging dies move toward and away from each other in association with a rotation of the cam;

suture guide members provided between the insertion means and the swaging dies, the suture guide members each having a concavity configured and disposed so as to form a tapered guide hole when the suture guide members are brought in contact with each other, the tapered guide hole having a diameter decreasing along the suture insertion direction toward the insertion hole of the needle; and the suture guide members being mounted on respective ones of the die support members such that the suture guide members are positioned in one of in contact or in close proximity with each other when the die support members are at the pre-swaging position.

34. An apparatus for manufacturing a needle attached suture in which an end of a needle is swaged with a lead end of a suture inserted in an insertion hole formed in the end of the needle to combine the suture with the needle, the apparatus comprising:

needle retaining means for holding the needle with at least the end thereof protruding from the needle retaining means;

insertion means for inserting the lead end of the suture into the insertion hole of the needle held by the needle retaining means by transporting the lead end in a suture insertion direction;

swaging dies for swaging the end of the needle at a swaging position by moving from substantially opposing swaging directions to swage the end of the needle with the suture inserted in the insertion hole of the needle to fix the suture in the insertion hole;

die support members for respectively supporting the swaging dies, said die support members having said swaging dies respectively mounted thereon and said die support members being rotatably coupled together to permit movement of said die support members relative each other in said opposing swaging directions;

swaging drive means for moving the die support members relatively toward and away from each other along the substantially opposing swaging directions to move the die support members and the swaging dies between a pre-swaging die position whereat the swaging dies are positioned in one of contact or close proximity with the end of the needle which is in an unswaged state and a swaging position whereat the swaging dies are positioned to swage the end of the needle;

suture guide members provided between the insertion means and the swaging dies, the suture guide members each having a concavity configured and disposed so as to form a tapered guide hole when the suture guide members are brought in contact with each other, the tapered guide hole having a diameter decreasing along the suture insertion direction toward the insertion hole of the needle; and the suture guide members being mounted on respective ones of the die support members such that the suture guide members are positioned in one of in contact or in close proximity with each other when the die support members are at the pre-swaging position.

35. The apparatus according to claim 34, further comprising swaging control means for controlling the swaging drive means to position the die support members at a first position apart from one another, at the pre-swaging position before the end of the needle is swaged, and at the swaging position whereat the end of the needle is swaged.

36. The apparatus according to claim 35, wherein:
the die support members have first ends and second ends with said swaging dies respectively mounted proximate said first ends;
the die support members are rotatably coupled together about an axis of rotation to permit relative movement of the die support members toward and away from each other, the axis of rotation being positioned between said first ends and said second ends of the die support members;
the swaging drive means includes a cam interposed between the die support members at a position between the axis of rotation and the second ends of the die support members, and cam drive means for rotating the cam; and
the cam being configured such that the swaging dies move toward and away from each other in association with a rotation of the cam.

37. The apparatus according to claim 36, wherein an axis of rotation extends in a direction parallel to the suture insertion direction.

38. The apparatus according to claim 34, wherein at least one of the die support members defines a groove extending in the needle swaging direction in which the adjustable swaging die is fitted to restrict a displacement of the adjustable swaging die in a direction orthogonal to the needle swaging direction and permit displacement in the needle swaging direction.

39. An apparatus for manufacturing a needle attached suture in which an end of a needle is swaged with a lead end of a suture inserted in an insertion hole formed in the end of the needle to combine the suture with the needle, the apparatus comprising:
needle retaining means for holding the needle with at least the end thereof protruding from the needle retaining means;
insertion means for inserting the lead end of the suture into the insertion hole of the needle held by the needle retaining means by transporting the lead end in a horizontal suture insertion direction;
swaging dies for swaging the end of the needle at a swaging position by moving from substantially opposing swaging directions to swage the end of the needle with the suture inserted in the insertion hole of the needle to fix the suture in the insertion hole;
die support members for respectively supporting the swaging dies, said die support members having said swaging dies respectively mounted thereon and said die support members being moveably coupled together to permit movement of said die support members relative each other in said opposing swaging directions;
swaging drive means for moving the die support members relatively toward and away from each other along the substantially opposing swaging directions to move the die support members and the swaging dies between a pre-swaging die position whereat the swaging dies are positioned in one of contact or close proximity with the end of the needle which is in an unswaged state and a swaging position whereat the swaging dies are positioned to swage the end of the needle;
suture guide members provided between the insertion means and the swaging dies, the suture guide members each having a concavity configured and disposed so as to form a tapered guide hole when the suture guide members are brought in contact with each other, the tapered guide hole having a diameter decreasing along the horizontal suture insertion direction toward the insertion hole of the needle; and
the suture guide members being mounted on respective ones of the die support members such that the suture guide members are positioned in one of in contact or in close proximity with each other when the die support members are at the pre-swaging position.

40. The apparatus according to claim 39, further comprising:
load supplier means for loading a specified stationary load on the suture combined with the needle in a state that the needle retaining means holds the needle while the specified stationary load is supported on the suture;
the needle retaining means holding the needle with the needle end aligned in the horizontal suture insertion direction;
the load supplier means including:
a weight member having a weight corresponding to the specified stationary load;
weight link means for linking the weight member to the suture while the suture hangs in a vertical direction;
suture manipulator means for lifting an intermediate portion of the suture to a level substantially horizontal and aligned with a swaged portion of the suture and the needle; and
weight release means for supporting the weight member when the weight link means initially links the weight member to the suture and for gradually removing support of the weight member to permit the specified stationary load of the weight member to be supported by the suture.

41. The apparatus according to claim 39, further comprising:
load supplier means for loading a specified stationary load on the suture combined with the needle in a state that the needle retaining means holds the needle while the specified stationary load is supported on the suture;
the needle retaining means holding the needle with the needle end aligned in the horizontal suture insertion direction;
the load supplier means including:
a weight member having a weight corresponding to the specified stationary load;
weight link means for linking the weight member to the suture in a state not supported by the suture while the suture hangs in a vertical direction; and
suture manipulator means for setting the weight member from a supported state where the weight member is supported on a base member to a hung state by lifting an intermediate portion of the suture upward to gradually hang the weight member above the base member.

42. An apparatus for manufacturing a needle attached suture in which an end of a needle is swaged with a lead end of a suture inserted in an insertion hole formed in the end of the needle to combine the suture with the needle, the apparatus comprising:
needle retaining means for holding the needle with at least the end thereof protruding from the needle retaining means;
insertion means for inserting the lead end of the suture into the insertion hole of the needle held by the needle retaining means by transporting the lead end in a horizontal suture insertion direction;

swaging dies for swaging the end of the needle at a swaging position by moving from substantially opposing swaging directions to swage the end of the needle with the suture inserted in the insertion hole of the needle to fix the suture in the insertion hole, said swaging dies being supported to permit movement of said swaging dies relative each other in said opposing swaging directions;

swaging drive means for moving the swaging dies relatively toward and away from each other along the substantially opposing swaging directions to move the swaging dies between a pre-swaging die position whereat the swaging dies are positioned in one of contact or close proximity with the end of the needle which is in an unswaged state and a swaging position whereat the swaging dies are positioned to swage the end of the needle;

load supplier means for loading a specified stationary load on the suture combined with the needle in a state that the needle retaining means holds the needle while the specified stationary load is supported on the suture;

the needle retaining means holding the needle with the needle end aligned in the horizontal suture insertion direction;

the load supplier means including:
  a weight member having a weight corresponding to the specified stationary load;
  weight link means for linking the weight member to the suture while the suture hangs in a vertical direction;
  suture manipulator means for lifting an intermediate portion of the suture to a level substantially horizontal and aligned with a swaged portion of the suture and the needle; and
  weight release means for supporting the weight member when the weight link means initially links the weight member to the suture and for gradually removing support of the weight member to permit the specified stationary load of the weight member to be supported by the suture.

43. An apparatus for manufacturing a needle attached suture in which an end of a needle is swaged with a lead end of a suture inserted in an insertion hole formed in the end of the needle to combine the suture with the needle, the apparatus comprising:

needle retaining means for holding the needle with at least the end thereof protruding from the needle retaining means;

insertion means for inserting the lead end of the suture into the insertion hole of the needle held by the needle retaining means by transporting the lead end in a horizontal suture insertion direction;

swaging dies for swaging the end of the needle at a swaging position by moving from substantially opposing swaging directions to swage the end of the needle with the suture inserted in the insertion hole of the needle to fix the suture in the insertion hole, said swaging dies being supported to permit movement of said swaging dies relative each other in said opposing swaging directions;

swaging drive means for moving the swaging dies relatively toward and away from each other along the substantially opposing swaging directions to move the swaging dies between a pre-swaging die position whereat the swaging dies are positioned in one of contact or close proximity with the end of the needle which is in an unswaged state and a swaging position whereat the swaging dies are positioned to swage the end of the needle;

load supplier means for loading a specified stationary load on the suture combined with the needle in a state that the needle retaining means holds the needle while the specified stationary load is supported on the suture;

the needle retaining means holding the needle with the needle end aligned in the horizontal suture insertion direction;

the load supplier means including:
  a weight member having a weight corresponding to the specified stationary load;
  weight link means for linking the weight member to the suture in a state not supported by the suture while the suture hangs in a vertical direction; and
  suture manipulator means for setting the weight member from a supported state where the weight member is supported on a base member to a hung state by lifting an intermediate portion of the suture upward to gradually hang the weight member above the base member.

* * * * *